US010411109B2

(12) United States Patent
Reznicek et al.

(10) Patent No.: US 10,411,109 B2
(45) Date of Patent: Sep. 10, 2019

(54) BIPOLAR JUNCTION TRANSISTOR (BJT) FOR LIQUID FLOW BIOSENSING APPLICATIONS WITHOUT A REFERENCE ELECTRODE AND LARGE SENSING AREA

(71) Applicant: INTERNATIONAL BUSINESS MACHINES CORPORATION, Armonk, NY (US)

(72) Inventors: Alexander Reznicek, Troy, NY (US); Tak H. Ning, Yorktown Heights, NY (US); Sufi Zafar, Briarcliff Manor, NY (US); Oscar van der Straten, Guilderland Center, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/860,067

(22) Filed: Jan. 2, 2018

(65) Prior Publication Data

US 2019/0207011 A1  Jul. 4, 2019

(51) Int. Cl.
*H01L 29/66* (2006.01)
*H01L 29/732* (2006.01)

(52) U.S. Cl.
CPC ...... *H01L 29/66234* (2013.01); *H01L 29/732* (2013.01)

(58) Field of Classification Search
CPC .......... H01L 29/66234; H01L 29/732; G01N 33/50–98
USPC .............................. 257/48; 436/501; 438/501
See application file for complete search history.

(56) References Cited

U.S. PATENT DOCUMENTS

| 9,625,409 | B1 * | 4/2017 | Cai ..................... G01N 27/26 |
| 9,714,952 | B2 * | 7/2017 | Feller ..................... G01N 33/84 |
| 9,857,328 | B2 * | 1/2018 | Hoffman ........... H01L 21/76883 |
| 2014/0027871 | A1 * | 1/2014 | Cai ........................ H01L 31/115 |
| | | | 257/431 |
| 2016/0011216 | A1 * | 1/2016 | Feller ..................... G01N 33/84 |
| | | | 436/501 |
| 2017/0059514 | A1 * | 3/2017 | Hoffman ............ G01N 33/5438 |
| 2017/0227556 | A1 * | 8/2017 | Feller ..................... G01N 33/84 |

OTHER PUBLICATIONS

Zafar, S. et al., "A comparison between bipolar transistor and nanowire field effect transistor biosensors" Applied Physics Letters (Feb. 2015) pp. 063701-1-063701-4, vol. 106.

* cited by examiner

*Primary Examiner* — Victoria K. Hall
(74) *Attorney, Agent, or Firm* — Tutunjian & Bitetto, P.C.; L. Jeffrey Kelly

(57) ABSTRACT

A bipolar junction transistor (BJT) containing sensor that includes a vertically oriented stack of an emitter overlying a supporting substrate, a base region present directly atop the emitter and a collector atop the base region. A first extrinsic base region is in contact with a first sidewall of a vertically oriented base region. The first extrinsic base region is electrically contacted to provide the bias current of the bipolar junction transistor during sensor operation. A second extrinsic base region is in contact with a second sidewall of the base region. The second extrinsic base region includes a sensing element. A sample trench is present adjacent to the BJT having a trench sidewall provided by the sensing element.

20 Claims, 19 Drawing Sheets

BIPOLAR JUNCTION TRANSISTOR (BJT) FOR LIQUID FLOW BIOSENSING APPLICATIONS WITHOUT A REFERENCE ELECTRODE AND LARGE SENSING AREA

BACKGROUND

Technical Field

The present invention generally relates to sensors, and more particularly to sensors including bipolar junction transistors.

Description of the Related Art

Mobile (portable and wearable) sensing technologies can non-invasively monitor health using bio-fluids such as sweat, saliva, urine have the potential to provide cost effective and enhanced healthcare, particularly in the treatment of chronic diseases which places heavy burden on societies. To develop mobile sensing technology, sensors are needed that can provide accurate data in a mobile setting. Hence, sensors may be desired to have robust and simple calibration, high sensitivity, low noise, low power requirements, miniaturized and can be cost effectively mass produced.

SUMMARY

In accordance with an embodiment of the present disclosure, a bipolar junction transistor (BJT) containing sensor is provided that includes a vertically oriented stack of an emitter overlying a supporting substrate, a base region present directly atop the emitter and a collector atop the base region. A first extrinsic base region is in contact with a first sidewall of a vertically orientated base region. The first extrinsic base region is electrically contacted to provide the bias current of the bipolar junction transistor during sensor operation. A second extrinsic base region in contact with a second sidewall of the base region, the second extrinsic base region including a sensing element. The device may further include a sample trench having a trench sidewall provided by the sensing element.

In another embodiment, the sensor may include a sensor composed of a sample trench. The sensor further includes a first vertically oriented bipolar junction transistor doped to a first conductivity type. The first vertically oriented bipolar junction transistor having a first sensing a surface of an extrinsic base region provides a first sidewall of the sample trench. A second vertically orientated bipolar junction transistor doped to a second conductivity type having a second a sensing surface of an extrinsic base region provides a second sidewall of the sample trench.

In yet another aspect, a method of forming a sensor is provided. The method of forming a sensor may include forming a bipolar junction transistor including a vertically oriented base region, and a two component extrinsic base region. The method may further include forming a sensor surface on a sidewall of a first component of the extrinsic base that is opposite a sidewall of the first component of the extrinsic base that is in contact with the vertically oriented base region. The method may further include forming a sample trench having a sidewall provide by the sensor surface.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Figure 1:
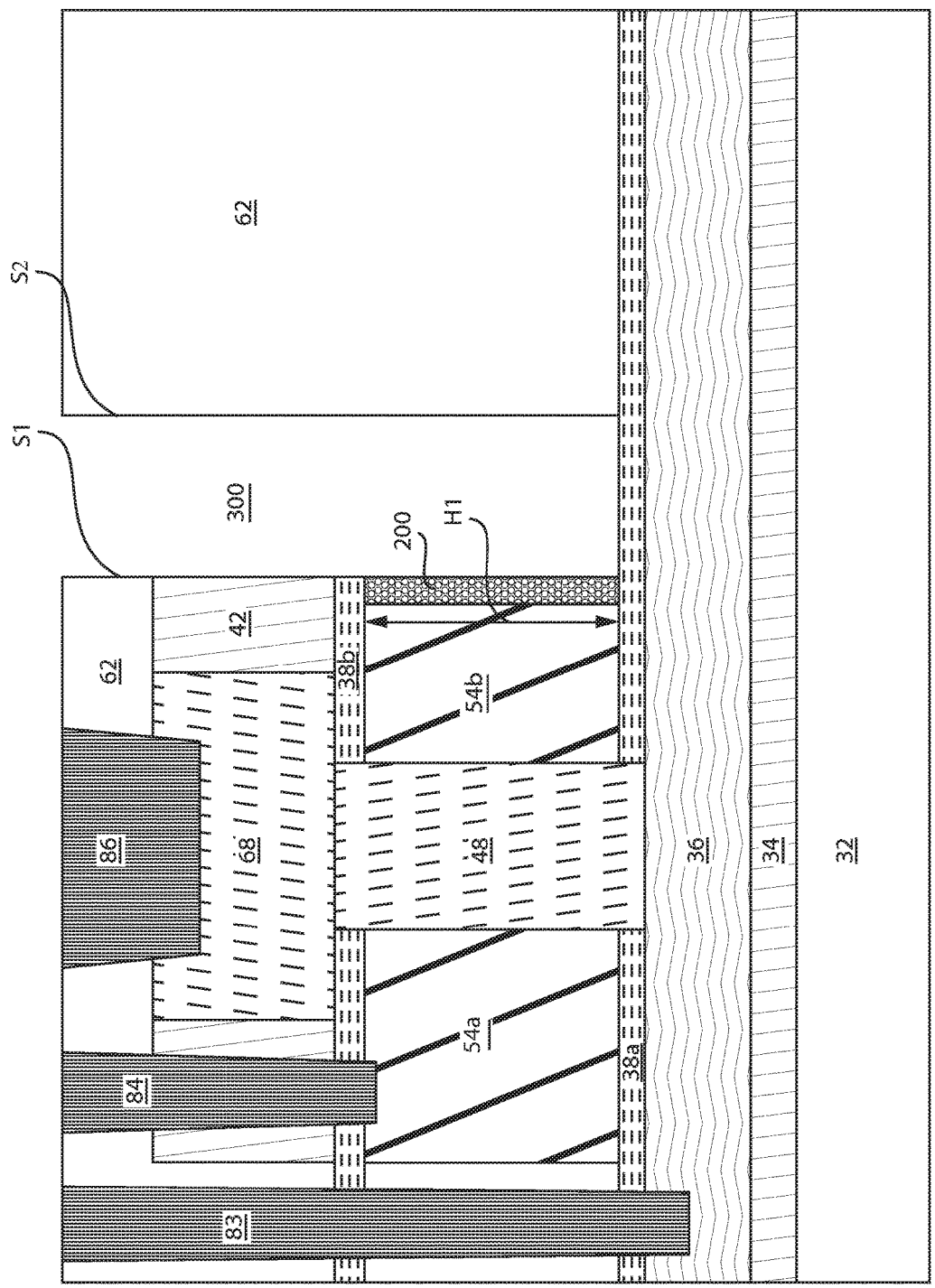
FIG. 1 is a side cross-sectional view depicting a bipolar junction transistor (BJT) containing sensor that includes a vertically oriented base region, a portion of an extrinsic base region that includes a sensing element, and a sample trench having a trench sidewall provided by the sensing element, in accordance with one embodiment of the present disclosure.

Detailed embodiments of the claimed structures and methods are disclosed herein; however, it is to be understood that the disclosed embodiments are merely illustrative of the claimed structures and methods that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure. For purposes of the description hereinafter, the terms "upper", "lower", "right", "left", "vertical", "horizontal", "top", "bottom", and derivatives thereof shall relate to the embodiments of the disclosure, as it is oriented in the drawing figures. The terms "positioned on" means that a first element, such as a first structure, is present on a second element, such as a second structure, wherein intervening elements, such as an interface structure, e.g. interface layer, may be present between the first element and the second element. The term "direct contact" means that a first element, such as a first structure, and a second element, such as a second structure, are connected without any intermediary conducting, insulating or semiconductor layers at the interface of the two elements.

Mobile (portable and wearable) sensing technologies can non-invasively monitor health using bio-fluids such as sweat, saliva, urine have the potential to provide cost effective and enhanced healthcare, particularly in the treatment of chronic diseases which places a heavy burden on societies. In some embodiments, bipolar junction transistors (BJT) sensors are better suited for mobile sensing applications than FET sensors because BJT sensors can have a simpler and more robust calibration; sensitivity and signal to noise ratio (SNR) in BJT sensors can be independent of applied voltages; and in BJT sensors it is possible to have the sub-threshold swing (measure of sensitivity) be the same for various devices. BJT sensors can also have a higher sensitivity and SNR in comparison to FET sensors.

The sensor structure and methods described herein employ a vertical bipolar transistor design having a large base area which is easily accessible from the sensing side to create a very large sensing area as compared to prior art. Increasing the contact area to measuring solution will reduce the noise and increase SNR, and decrease response time. In some embodiments, the design of the BJT sensors of the present disclosure provides a base contact on one side of the base, with the other side being free to measure the potential of the flowing solution that can be present in a sample trench. This leads to elimination of reference electrode as used in prior devices. In some embodiments, the sample liquid being sensed by the BJT containing sensor will be pumped and flow in a horizontal manner in a trench, where one or both sidewall of the trench are BJT sensing areas. In some embodiments, the methods and structures provided herein can provide one, two or multiple BJT's along a trench enabling measurements of multiple properties of DNA or proteins at the same time. Lowest noise for III-V BJT would be using an InP emitter (wider bandgap=lower noise), or for group IV based semiconductors a Si—SiGe—Si structure. The methods and structures of the present disclosure are now described with more detail with reference to FIGS. 1-19.

Figure 2:
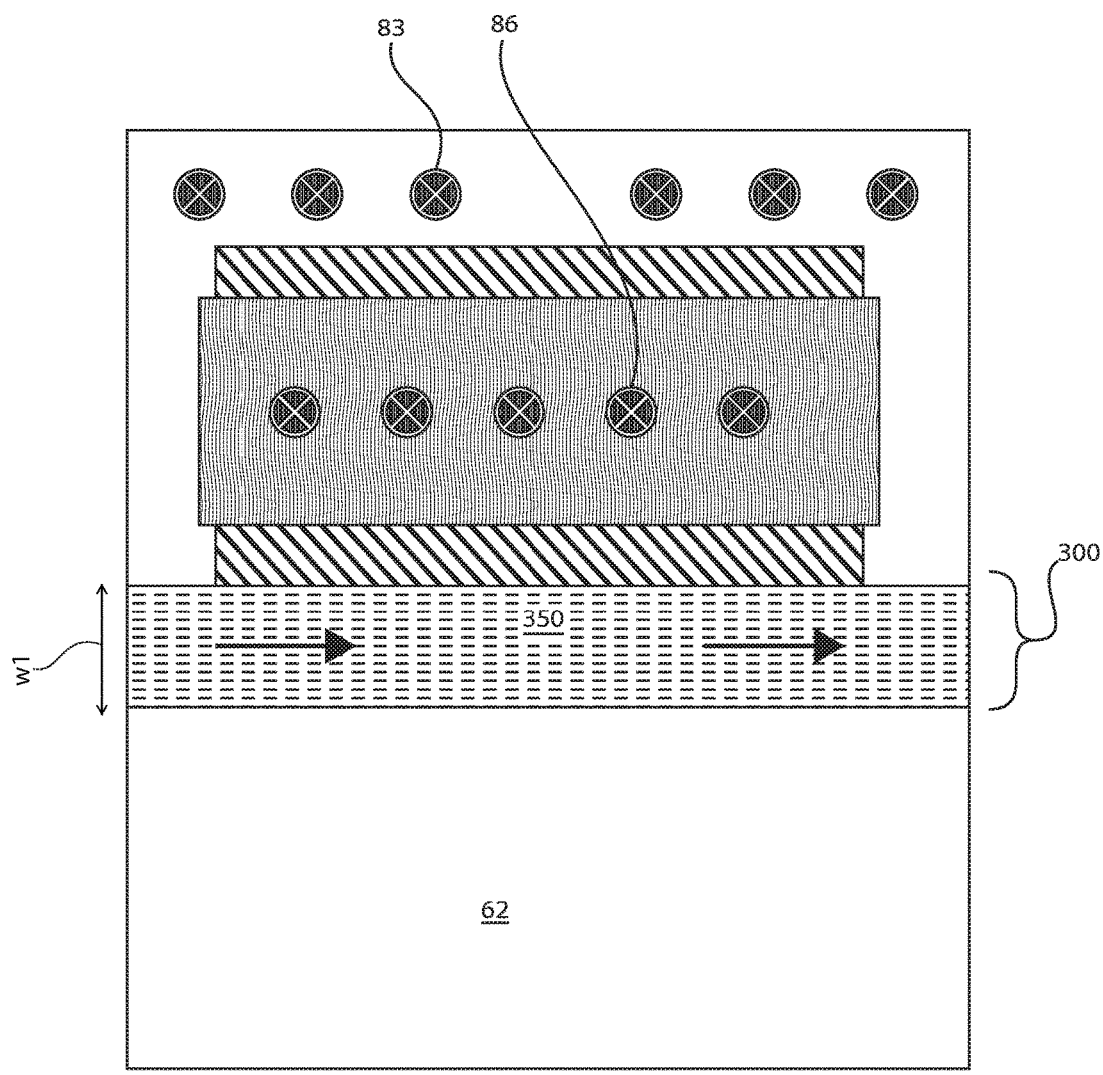
FIG. 2 is a top down view of the structure depicted in FIG. 1.

FIGS. 1 and 2 depicts a bipolar junction transistor (BJT) containing sensor that includes a vertically oriented base region 48, a portion of an extrinsic base region 54b that includes a sensing element, and a sample trench 300 having a trench sidewall provided by the sensing element 200. The extrinsic base region 54a, 54b includes two portions. The left portion, i.e., first portion 54a, of the extrinsic base is physically separate from the right portion, i.e. second portion 54b, of the extrinsic base, and hence are not electrically connected. The first portion 54a of the extrinsic base region, i.e., base contact, can be used to set the bias current of the transistor during sensing operations. The first portion 54a of the extrinsic base region may provide the metal base contact. The second portion 54b of the extrinsic base portion, which is the side of the bipolar junction transistor adjacent to the sample trench 300, has a sensing surface. The second portion 54b of the extrinsic base portion is physically separate from the metal base contact. The sensing surface 200 may extends along an entire height H1 of the extrinsic base 54a, 54b. The sensing surface 200 extends continuously along the entire height H1 of the extrinsic base 54a, 54b and can have a uniform width without any breaks in continuity.

The vertical bipolar junction transistor (BJT) has a base contact (contact to the first portion 54a of the epitaxial base region 54a) on one side of the BJT, whereas the opposing side of the BJT is free to measure the potential of the solution, which may be a flowing solution, that is present in the sample trench 300. The device configuration depicted in FIGS. 1 and 2, allows for the elimination of reference electrodes, as used in prior designs. This provides an advantage because integration of reference electrodes on semiconductor chips, such as silicon chips, can be difficult. Further, reference electrodes degrade with use, and therefore can have reliability issues.

The sensing measurement of a sample within the sample trench 300 will be made as follows. Emitter voltage will be ramped or held at constant. For example, the voltage applied to the emitter 36 through the emitter contact 83 will be ramped or held at a constant value of 1 volt or less (<|1|V). The collector voltage will be set to 0. For example, the voltage applied to the collector 68 through the collector contact 86 can be set to 0. The base terminal can be set at a fixed voltage, and the base current flows through it. For example, the voltage applied to the base, applied to the first portion 54a of the extrinsic base region, through the base contact 84 can be set at a fixed value, e.g., set at a fixed voltage of 1 volt or less (<|1|V), and the base current will flow through it. The presence of the base contact eliminates the need for a reference electrode. The charges bound to the oxide layer on top of the base can capacitively couple the base, and modulate the sensing collector current.

FIGS. 1 and 2 depict a sensor including an exemplary single column compound semiconductor bipolar junction transistor (BJT) on a semiconductor surface 32, such as a III-V semiconductor substrate or a type IV semiconductor substrate. The term "bipolar junction transistor (BJT)" denotes is a semiconductor device formed by two P-N junctions whose function is amplification of an electric current. Bipolar transistors are made from 3 sections of semiconductor material, i.e., alternating P-type and N-type conductivity semiconductor materials, with two resulting P-N junctions. As will be described in greater detail below the (BJT) devices disclosed herein are vertical bipolar junction transistors (VBJT). The term "vertical" as used to describe a BJT device denotes that means that the dimension extending from the beginning of the emitter 36 through the base 48 to the collector 68 is vertically orientated or is perpendicular relative to the upper surface of the substrate 32. The term "III-V semiconductor" denotes a semiconductor material that includes at least one element from Group III of the Periodic Table of Elements and at least one element from Group V of the Periodic Table of Elements. Typically, the III-V compound semiconductors are binary, ternary or quaternary alloys including III/V elements. In contrast to type III-V semiconductor materials, by "type IV semiconductor" it is meant that the semiconductor material includes at least one element from Group IVA (i.e., Group 14) of the Periodic Table of Elements.

In some embodiments, the bipolar junction transistor containing sensor includes a vertically oriented stack of an emitter 36 overlying a supporting substrate 32, a base region 48 present directly atop the emitter 36 and a collector 68 atop the base region 48. The base region 48 is the region of the device that is present between the emitter 36 and the collector 68 of a transistor and into which minority carriers are injected. The collector 68 is a region of the transistor through which a primary flow of charge carriers leaves the base 48. In some embodiments, the emitter 36 is a region from which charge carriers that are minority carriers in the base are injected into the base.

Each of the emitter 36, the base 48 and the collector 68 may be composed of a semiconductor material, such as a type III-V semiconductor material, e.g., InGaAs and/or InGaAlAs, or a type IV semiconductor material, such as silicon. The emitter 36 and the collector 68 have a dopant conductivity, e.g., n-type that is opposite the conductivity type of the base region, e.g., p-type. In one example, the collector 68 is composed of large grain polycrystalline silicon having a n-type conductivity, the base 48 is composed of InGaAs and/or InGaAlAs having a p-type conductivity, and the emitter 36 is composed of InGaAs and/or InGaAlAs having an n-type conductivity. It is noted that in some instances a silicon or silicon germanium material may be substituted for the aforementioned type III-V semiconductor materials that are provided for the emitter region and the base region.

The extrinsic base region having the first and second portions 54a, 54b is typically composed of a same conductivity type dopant as the base region 48, but the conductivity type dopant in the first and second portions 54a, 54b of the extrinsic base region is present in a higher concentration than the concentration type dopant in the base region 48. Similar to the emitter 36, the base 48 and the collector 68, the extrinsic base region 54a, 54b may be composed of a semiconductor material, such as a type III-V semiconductor material, e.g., InGaAs and/or InGaAlAs, or a type IV semiconductor material, such as silicon. In one example, the extrinsic base region 54a, 54b may be composed of large grain polysilicon having a p-type conductivity.

The emitter-collector distance is the height of the physical base region 48. The height of the physical base region 48 consists of three regions: (i) a space-charge region of the emitter-base diode, (ii) a space-charge region of the collector-base diode, and (iii) a quasi-neutral base region sandwiched between the two space-charge regions. In some embodiments, it is the quasi-neutral base region that controls the current flow from emitter to the collector, and the height (base width) and doping concentration of the quasi-neutral base region that determined the magnitude of the collector current for a given emitter base bias voltage. As an example, for a base doping concentration of $5 \times 10^{18}$ cm$^{-3}$, and a target width of 20 nm for the quasi-neutral base region, the emitter-collector distance should be about 55 nm.

In some embodiment, a first portion of the extrinsic base region 54a is in contact with a first sidewall of a vertically oriented base region 48. The first portion of the extrinsic base region 54a is electrically contacted to provide the bias current of the bipolar junction transistor during sensor operation. The bias current is applied to the first portion of the extrinsic base region 54a through a base contact 84. In some embodiments, a second extrinsic base region 54b is in contact with a second sidewall of the vertically orientated base region 48. The second portion of the extrinsic base region 54b includes a sensing element 200. The sensing element 200 provides the sidewall of the sample trench 300 that is adjacent to the BJT sensor.

As noted above, the sensing element 200 extends along an entire height H1 of the second portion of the extrinsic base region 54b. The composition of the sensing element 200 may be selected for the application of the sensor. For example, in one embodiment, the sensing element is a titanium nitride (TiN) layer, in which the sensing element 200 is for sensing pH of a sample within the sample trench 300. In another example, the sensing element 200 is composed of a silver chloride (AgCl) layer, in which the sensing element 200 is for sensing chloride (Cl) content of a sample within the sample trench 300. In yet another example, the sensing element 200 is composed of gold (Au). A sensing element that is provided by a gold (Au) layer may be used for sensing DNA, as well as proteins using this chemistry.

Still referring to FIGS. 1-2, the BJT sensor also includes a plurality of dielectric layers. For example, a bottom spacer 38a may separate the first and second portions of the extrinsic base region 54a, 54b from the emitter 36. An upper spacer 38b may separate the collector 68 from the first and second portions of the extrinsic base region 54a, 54b. A collector level dielectric 42 may be present atop the upper spacer 38b, and the collector level dielectric 42 may have an upper surface that is coplanar with the upper surface of the collector region 68. In one embodiment, the collector level dielectric 42 is composed of silicon oxide (SiO$_2$). An interlevel dielectric layer (ILD) 62 is present atop the BJT.

The sample trench 300 is formed through the interlevel dielectric layer 62, in which a first sidewall S1 of the sample trench 300 includes a portion of the sensing surface 200 (also referred to as sensing surface layer), and a second sidewall S2 of the sample trench 300 is entirely provided by the interlevel dielectric layer (ILD) 62. Referring to FIG. 1, the sensing surface 200 provides the lower portion of the first sidewall S1 of the sample trench 300, while the upper portion of the first sidewall S1 of the sample trench 300 is provided by a portion of the interlevel dielectric layer (ILD) 62. The portion of the interlevel dielectric layer (ILD) 62 and the sensing surface 200 that provides the first sidewall S1 of the sample trench 300 are aligned to one another.

In some embodiments, contacts 83, 84, 86 are formed through the ILD layer 62 and the collector level dielectric 42. An emitter contact 83 may be present within a via extending through the interlevel dielectric layer 62 and the lower spacer 38a to provide that the emitter contact 83 is in direct contact with the emitter layer 36. A base contact 84 may be present within a via extending through the interlevel dielectric layer 62, the collector level dielectric 42, and the upper spacer layer 38b to provide that the base contact 84 is in direct contact with the first portion of the extrinsic base region 54a. A collector contact 86 may extend through the interlevel dielectric layer 62 into direct contact with the collector 68.

Referring to FIGS. 1 and 2, the sample trench 300 is positioned for horizontal sensing. In the embodiment that is depicted in FIGS. 1 and 2, the sensing BJT is present on one side of the sample trench 300. FIG. 2 is a down view of a BJT sensor including a horizontally positioned sample trench 300 and a single BJT having a single sensing surface 200 providing a sidewall of the sample trench 300. The direction of flow of the sample 350 being sensed within the sample trench 300 is identified by the arrow. The width W1 of the sample trench 300 may be selected in accordance with the sample from which the measurements are being taken. For example, some DNA molecules within the sample 350 may have a maximum dimension (i.e., largest dimension characterizing a single DNA molecule), e.g., length or diameter, that is 3 Å. Some small proteins that may be sensed from the sample 350 may have a maximum dimension (i.e., largest dimension characterizing a single protein), e.g., diameter, ranging from 50 Å to 100 Å. Some enzymes that can be sensed from the sample 350 within the sample trench 300 of the BJT sensor can have a maximum dimension (i.e., largest dimension characterizing a single DNA molecule), e.g., length or diameter, that is 400 Å.

The width W1 of the sample trench 300 may be selected to accommodate the above samples. In other examples, width W1 of the sample trench 300 may be as great as 5 microns for analyzing cancer cells. In yet other examples, the width W1 of the sample trench 300 may be as great as 100 nm for analyzing large proteins.

It is noted that the embodiment depicted above with reference to FIGS. 1 and 2 that includes a single BJT device on one side of the sample trench 300 is only one example of a sensor in accordance with the methods and structures disclosed herein. In other embodiments, two BJTs of opposite polarity, i.e., opposite conductivity type, can be employed as a sensor, in which each BJT includes a sensing surface that provides a sidewall of a sample trench 300. For example, a first BJT being be a NPN device on a first side of the sample trench 300, and a second BJT being PNP on an opposing side of the sample trench 300. The sample trench 300 is overlying a shallow trench isolation (STI) region 600. The shallow trench isolation (STI) region 600 may be composed of an oxide, such as silicon oxide ($SiO_2$), and provides for isolation of the first vertically oriented bipolar junction transistor 400 from the second vertically orientated bipolar junction transistor 500.

Figure 3:
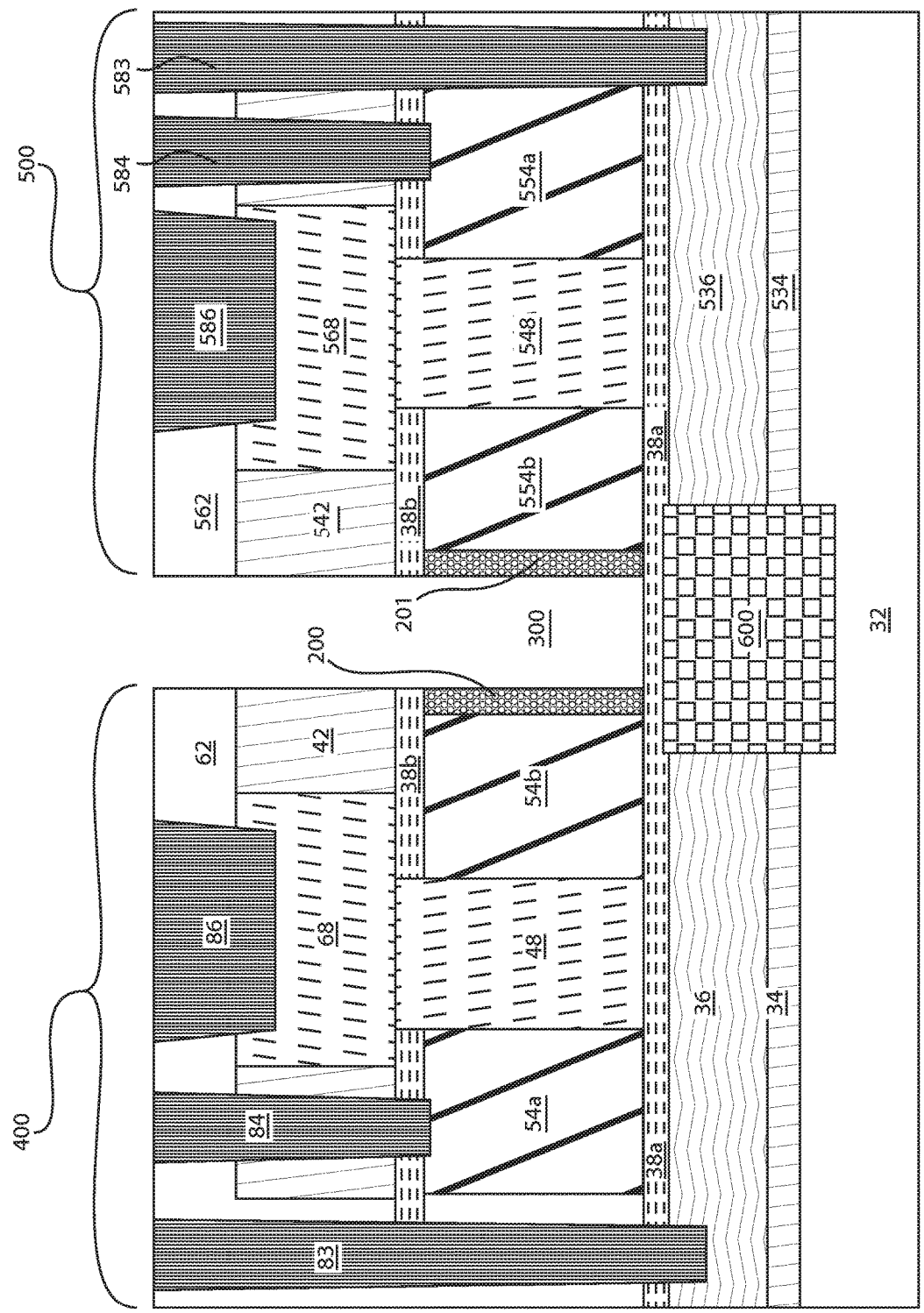
FIG. 3 is a side cross-sectional view of a bipolar junction transistor (BJT) containing sensor including a sample trench, in which the sensor further includes a first vertically oriented bipolar junction transistor doped to a first conductivity type having a first sensing surface of an extrinsic base region providing a first sidewall of the sample trench, and a second vertically oriented bipolar junction transistor doped to a second conductivity type having a second sensing surface of an extrinsic base region providing a second sidewall of the sample trench, in accordance with another embodiment of the present disclosure.

FIG. 3 depicts one embodiment of a sensor that includes a sample trench 300 and a first and second vertically oriented bipolar junction transistor 400, 500. The first vertically oriented bipolar junction transistor 400 may be an NPN transistor, and has been described above with reference to FIGS. 1 and 2. Each of the reference numbers designating structures in the first a vertically oriented bipolar junction transistor 400 have been described above in the description of structures having the same reference numbers with reference to FIGS. 1 and 2.

The second vertically oriented bipolar junction transistor 500 is similar to the first vertically oriented bipolar junction transistor 400 that is described with reference to FIGS. 1 and 2. For example, the emitter layer 536 that is depicted in FIG. 3 is similar to the emitter layer 36 depicted in FIG. 1. The emitter layer 36 depicted in FIG. 3 has an n-type conductivity for a first vertically oriented bipolar junction transistor 400 that is an NPN device, and the emitter layer 536 depicted in FIG. 3 has a p-type conductivity for the second vertically oriented bipolar junction transistor 500 that is a PNP device. Because of the p-type conductivity type of the emitter 536 for the second vertically orientated bipolar junction transistor 500, the underlying punch through stop layer/isolation layer 534 is doped to an n-type conductivity. The vertically oriented base 548 and the collector 568 of the second vertically oriented bipolar junction transistor 500 are also similar to the vertically oriented base 48 and the collector 68 that have been described above with reference to FIG. 1. The vertically oriented base region 48 depicted in FIG. 3 has a p-type conductivity for a first vertically oriented bipolar junction transistor 400 that is an NPN device, and the vertically oriented base region 548 depicted in FIG. 3 has an n-type conductivity for the second vertically oriented bipolar junction transistor 500 that is a PNP device. The collector region 68 depicted in FIG. 3 has an n-type conductivity for a first vertically oriented bipolar junction transistor 400 that is an NPN device, and the collector 568 depicted in FIG. 3 has a p-type conductivity for the second vertically oriented bipolar junction transistor 500 that is a PNP device.

The first vertically oriented bipolar junction transistor 400 includes an extrinsic base region that includes two components. A first portion 54a of the extrinsic base of the first vertically oriented bipolar junction transistor 400 is physically separate from a second portion 54b of the extrinsic base, and hence are not electrically connected. Similarly, the first portion 554a of the extrinsic base of the second vertically oriented bipolar junction transistor 500 is similarly separate from the second portion 554b of the extrinsic base of the second vertically oriented bipolar junction transistor 500. The first portion 54a, 554a of the extrinsic base region, i.e., base contact, for each of the first and second vertically oriented bipolar junction transistors 400, 500 can be used to set the bias current of those transistor during sensing operations. The second portion 54b, 554b of the extrinsic base portion for each of the vertically oriented bipolar junction transistors 400, 500 that is adjacent to the sample trench 300, has a sensing surface 200, 201. The sensing surface 200, 201 for each of the second portions 54b, 554b of the extrinsic base region for the first and second vertically oriented bipolar junction transistors 400, 500 may extend along an entire height H1 of the extrinsic base 54b, 554b. The sensing surface 200, 201 extend continuously along the entire height H1 of the extrinsic base 54b, 554b and can have a uniform width without any breaks in continuity.

In the embodiment depicted in FIG. 3, the sensing surface 200, 201 of the first and second vertically oriented bipolar junction transistors 400, 500 provides the opposing sidewalls of the sample trench 300, in which the first vertically oriented bipolar junction transistor 400 is positioned on one side of the sample trench 300, and the second vertically oriented bipolar junction transistor 500 is positioned on a second opposing side of the sample trench 300.

Each of the first sensing surface 200 and the second sensing surface 201 may have a composition selected from titanium nitride (TiN), silver chloride (AgCl), gold (Au) and combinations thereof. The application for the aforementioned compositions, i.e., what the compositions can sense from a sample 350 within the sample trench 300, have been described above with reference to FIGS. 1 and 2.

Figure 4:
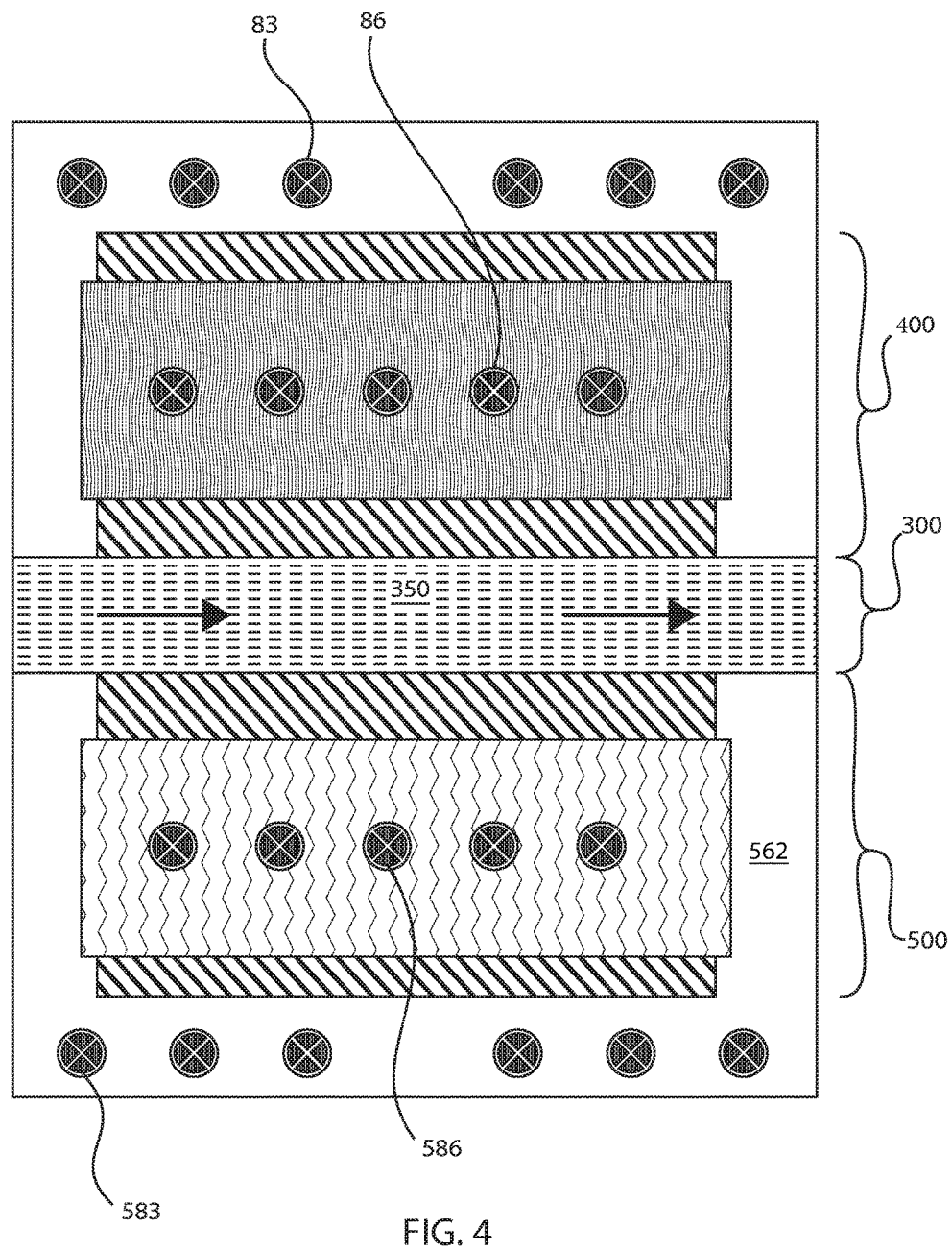
FIG. 4 is a top down view of structure depicted in FIG. 3.

Referring back to FIG. 3, the first and second vertically oriented bipolar junction transistors 400, 500 may further include a plurality of dielectric layers, such as interlevel dielectric layers 62, 562 and collector level dielectrics 42, 542 that are present on opposing sides of the sample trench 300. Each of the first and second vertically oriented bipolar junction transistors 400, 500 include a plurality of contacts 83, 84, 86, 583, 584, 586. Referring to FIGS. 3 and 4, the first vertically oriented bipolar junction transistor 400 may include an emitter contact 83, a base contact 84 and a collector contact 86. Referring to FIGS. 3 and 4, the second vertically oriented bipolar junction transistor 500 may include an emitter contact 583, a base contact 584 and a collector contact 586.

It is noted that in some embodiments, it is not necessary that the first vertically oriented a bipolar junction transistor 400 and the second vertically oriented bipolar junction transistor 500 have different conductivity types, i.e., different polarities. For example, in some embodiments both a the first vertically oriented bipolar junction transistor 400 and the second vertically oriented bipolar junction transistor 500 can be NPN transistors. In another example, both the first vertically a oriented bipolar junction transistor 400 and the second vertically oriented bipolar junction transistor 500 can be PNP transistors.

Figure 5:
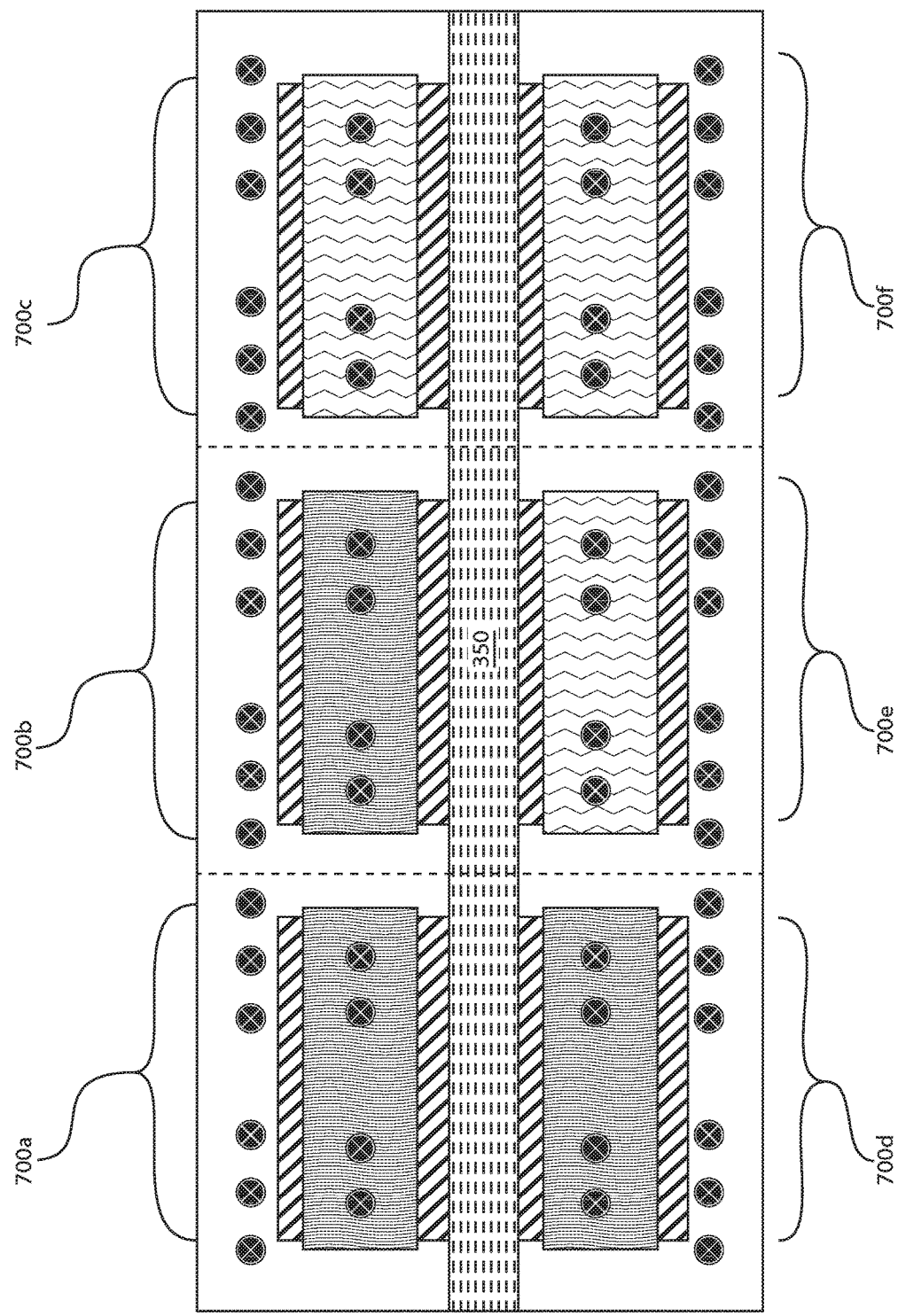
FIG. 5 is a top down view of a sensor including multiple BJT devices sensing along a sample trench.

It is also noted that it is not required that a multiple BJT sensor be only limited to two BJT devices, as depicted in FIGS. 3 and 4. FIG. 5 illustrates one embodiment of a sensor including multiple BJT devices 700a, 700b, 700c, 700d, 700e, 700f sensing along a single sample trench 300. Each of the BJT devices 700a, 700b, 700c, 700d, 700e, 700f that are depicted in FIG. 5 may be provided by one of the first and second vertically oriented bipolar junction transistors 400, 500 that have been described above with reference to FIGS. 1-4, and include a sensing surface 200, 201 that provides a portion of the sidewall of the sample trench 300.

Figure 6:
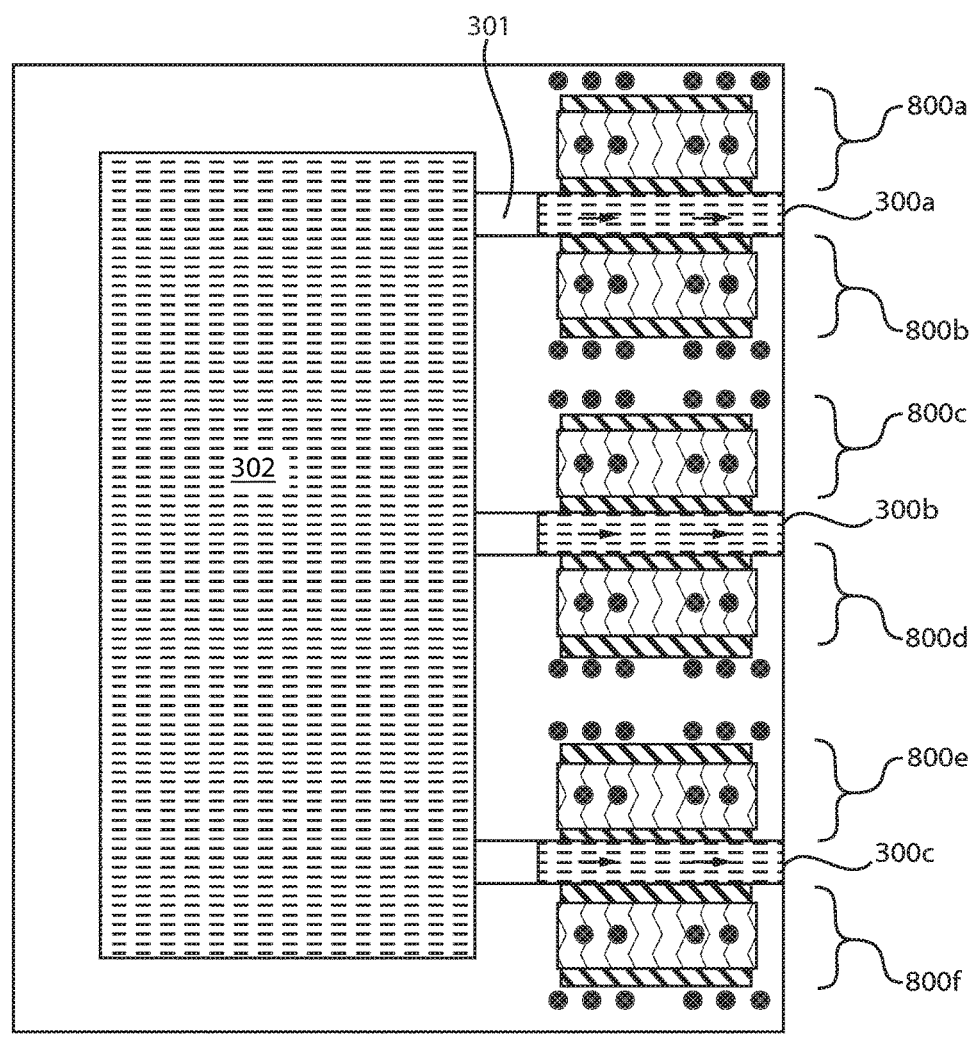
FIG. 6 is top down view depicting a sensor for parallel sensing of a sample within a sample reservoir using multiple BJT devices, in accordance with one embodiment of the present disclosure.

FIG. 6 depicts another embodiment of the present disclosure, which includes a sensor for parallel sensing of a sample within a sample reservoir 301 using multiple BJT devices 800a, 800b, 800c, 800d, 800e, 800f sensing along a single sample trench 300a, 300b, 300c. Each of the BJT devices 800a, 800b, 800c, 800d, 800e, 800f that are depicted in FIG. 6 may be provided by one of the first and second vertically oriented bipolar junction transistors 400, 500 that have been described above with reference to FIGS. 1-4, and include a sensing surface 200, 201 that provides a portion of the sidewall of the sample trench 300a, 300b, 300d. In the embodiment depicted in FIG. 6, the a sample reservoir 302 is pumped by micro-pumps 301 into three sample trenches 300a, 300b, 300c.

The structures depicted in FIGS. 1-6 are now described with greater detail with reference to FIGS. 7-19. It is noted that the process sequence depicted in FIGS. 7-19 can provide the structure depicted in FIGS. 1-2. The process sequence depicted in FIGS. 7-19 can also provide the structures depicted in FIGS. 3-6 using hard masks to independently process the different regions of a substrate, in which BJT devices and sample trenches are formed in accordance with the method described with reference to FIGS. 7-19.

Figure 7:
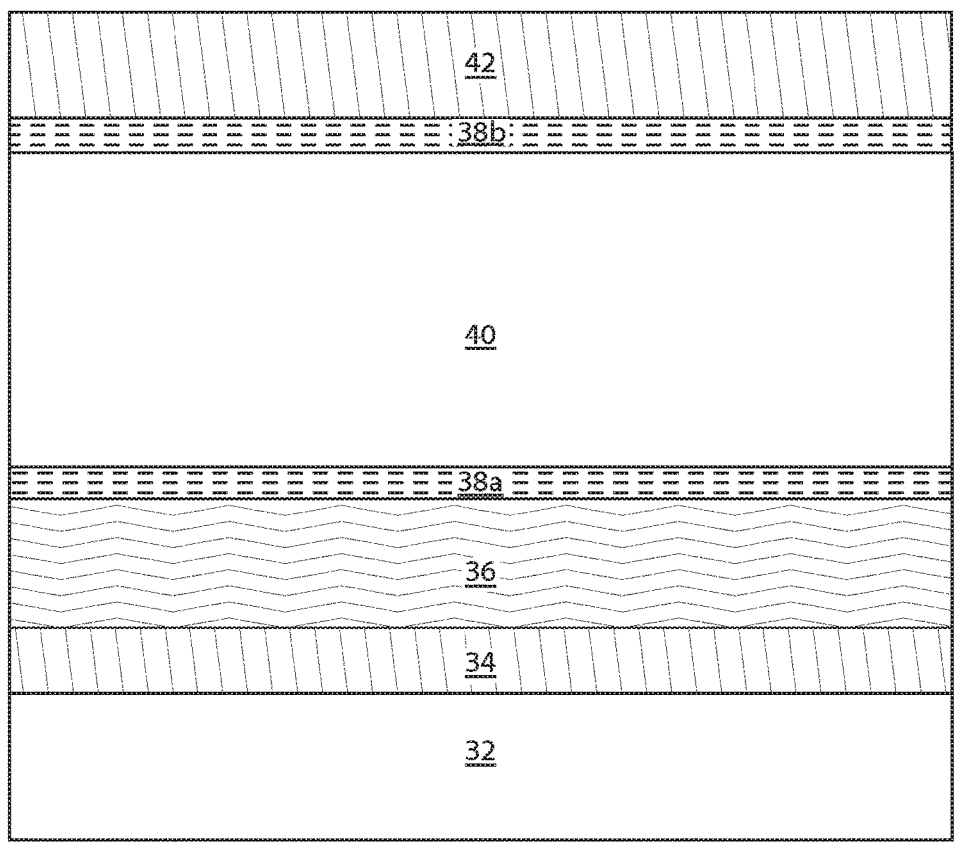
FIG. 7 is a side cross-sectional view showing a semiconductor substrate having compound semiconductor layers and dielectric layers thereon.

With reference now to FIG. 7, in some embodiments the BJT sensor is formed from a multi-layer structure includes a semiconductor substrate 32, such as a type III-V semiconductor substrate or type IV semiconductor substrate; a relatively wide bandgap semi-isolation layer 34; a heavily doped semiconductor layer 36, such as a heavily doped III-V semiconductor layer and/or a heavily doped type IV semiconductor, that may later function as a BJT emitter; bottom and top spacers 38a, 38b, a sacrificial layer 40 between the spacers, and a dielectric (e.g. oxide) layer 42 on the top spacer. In some embodiments, the substrate 32 has a surface portion of III-V compound semiconductor material that allows the subsequent epitaxial growth of III-V compound semiconductor materials thereon without the difficulties and problems associated with growing such material on substrates where a significant lattice mismatch would be present. The substrate 32 may alternatively comprise a relaxed III-V layer on a silicon wafer. In an exemplary embodiment, the III-V material comprising the substrate is InP. In yet another embodiment, the substrate 32 may be a type IV semiconductor, such as silicon (Si).

The layer 34 of semi-insulating material is epitaxially grown on the substrate 32. The terms "epitaxially growing and/or depositing" and "epitaxially grown and/or deposited" mean the growth of a semiconductor material on a deposition surface of a semiconductor material, in which the semiconductor material being grown has the same crystalline characteristics as the semiconductor material of the deposition surface. In an epitaxial deposition process, the chemical reactants provided by the source gases are controlled and the system parameters are set so that the depositing atoms arrive at the deposition surface of the semiconductor substrate with sufficient energy to move around on the surface and orient themselves to the crystal arrangement of the atoms of the deposition surface. Therefore, an epitaxial semiconductor material has the same crystalline characteristics as the deposition surface on which it is formed. In an exemplary embodiment using an InP substrate, the semi-isolating layer consists essentially of InAlAs.

The heavily doped III-V compound semiconductor layer 36 is epitaxially grown on the semi-isolating layer 34. The lattice constants of $In_{0.53}Ga_{0.47}As$, InAlAs ($In_{0.52}Al_{0.48}As$), and InP are substantially the same, allowing a high quality InGaAs layer to be grown on an InAlAs layer. The bandgap of InAlAs is substantially greater than the bandgap of InGaAs and is therefore capable of providing electrical isolation. The dopants in the semiconductor layer 36 may be incorporated in situ using appropriate precursors, as known in the art. In one exemplary embodiment, the heavily doped InGaAs layer has a doping concentration of 1e19-3e20 $cm^{-3}$ or greater and n-type conductivity. As used herein, the term "conductivity type" denotes a dopant region being p-type or n-type. As used herein, "p-type" refers to the addition of impurities to an intrinsic semiconductor that creates deficiencies of valence electrons. In a silicon-containing substrate, examples of p-type dopants, i.e., impurities include but are not limited to: boron, aluminium, gallium and indium. As used herein, "n-type" refers to the addition of impurities that contributes free electrons to an intrinsic semiconductor. Silicon can be used as an n-type or p-type dopant in III-V semiconductor materials. Other n-type dopants that can be used in III-V semiconductor materials include tellurium, tin and germanium while other p-type dopants include zinc and carbon. The thickness of the heavily doped III-V layer 36 may be in the range of 5 nm to 40 nm. A larger bandgap III-V compound semiconductor material (e.g. GaAs) can be employed for high voltage or power transistor applications. In an exemplary embodiment in which a heterojunction bipolar transistor is formed, the semiconductor layer 36 could consist essentially of InGaAlAs and function as an emitter. The inclusion of a small percentage of aluminium (Al) widens the bandgap. The percentage of indium (In) in the emitter of the heterojunction device can be a few percent higher than in the subsequently formed III-V base layer to compensate for lattice shrinkage due to the smaller size of the aluminium atom.

III-V compound semiconductors are obtained by combining group III elements (for example, Al, Ga, In) with group V elements (for example, N, P, As, Sb). GaAs, InGaAs, InP, GaP, and GaN are examples of III-V compound semiconductors. Many different III-V compounds could be grown on the substrate 32 and accordingly multiple precursors could be used. Depending on which III-V material(s) is to be grown and which precursor is used, different parameters (temperature, process pressure, times, etc.) are applicable. Metalorganic precursors include Trimethylgallium, Trimethylaluminum, Trimethylindium, Trimethylantimony, Tertiarybutylarsine and Tertiarybutylphosphine. Alternate Group V precursors include arsine and phosphine. Depending which Group V source is used, process temperature, gas flow, pressure and times vary significantly. The process parameters for growing III-V semiconductor materials on silicon and on other III-V semiconductor materials are well known in the art and new methods continue to be developed.

The bottom and top spacers 38a, 38b may be silicon nitride spacers. The bottom spacer 38a is deposited as a blanket layer on the doped epitaxial III-V layer 36. "Blanket" deposition refers to the deposition of the layer without masking of the underlying substrate material. The spacers can be deposited using directional deposition techniques including, but not necessarily limited to high density plasma (HDP) deposition and gas cluster ion beam (GCIB) deposition, or deposition techniques including, but not limited to, chemical vapor deposition (CVD), plasma enhanced CVD (PECVD), radio-frequency CVD (RFCVD), physical vapor deposition (PVD), atomic layer deposition (ALD), molecular layer deposition (MLD), molecular beam deposition (MBD), pulsed laser deposition (PLD), liquid source misted chemical deposition (LSMCD), and/or sputtering.

The sacrificial layer 40 deposited on the bottom spacer 38a may be an amorphous silicon (a-Si) or a polycrystalline silicon (polysilicon) layer that can be etched selectively to the spacer material. The sacrificial layer material may be deposited by a deposition process such as, but not limited to, physical vapor deposition (PVD), chemical vapor deposition (CVD), plasma enhanced chemical vapor deposition (PECVD), inductively coupled plasma chemical vapor deposition (ICP CVD), or any combination thereof. Hydrogenated amorphous silicon is typically deposited by plasma-enhanced chemical vapor deposition (PECVD) although other techniques such as hot-wire chemical vapor deposition (HWCVD) may be used. The top spacer 38b is deposited on the top surface of the sacrificial layer 40.

The oxide layer 42 is deposited on the top surface of the top spacer 38b. Non-limiting examples of materials for the oxide layer 42 include silicon dioxide, tetraethylorthosilicate (TEOS) oxide, high aspect ratio plasma (HARP) oxide, high temperature oxide (HTO), high density plasma (HDP) oxide, oxides (e.g., silicon oxides) formed by an atomic layer deposition (ALD) process, or any combination thereof. The oxide layer 42 has a thickness in a range from about one hundred to one thousand nanometers in some embodiments, though such a thickness range is not considered critical.

Figure 8:
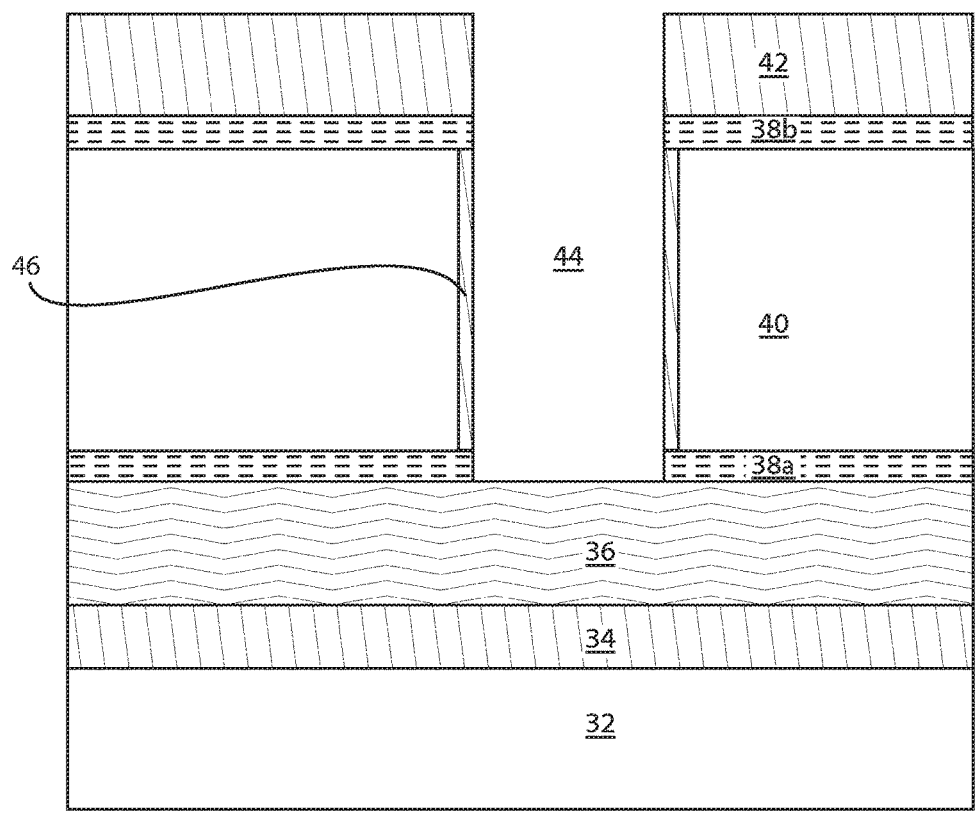
FIG. 8 is a side cross-sectional view depicting formation of a trench in the structure depicted in FIG. 7, formation of an oxide layer within the trench, and exposing a portion of an emitter layer.

As shown in FIG. 8, a trench 44 is formed in the structure depicted in FIG. 7. The etch process used to form the trench 44 may be, for example, a reactive ion etch (RIE) such that the trench includes substantially vertical side walls. Sequential RIE processes are employed to etch through the oxide layer 42, the top spacer 38b, and the sacrificial layer 40, respectively. The bottom spacer 38a functions as an etch stop following etching of the sacrificial layer 40. The trench 36 accordingly extends from the top surface of the oxide layer to the bottom spacer 38a. A patterned mask (not shown) having an opening corresponding to the trench location is formed on the top surface of the oxide layer 42 prior to etching the oxide material and the underlying layers. The mask protects the remainder of the structure. A trench 44 having a width between five and fifty nanometers can be formed in the fabrication of a bipolar junction transistor as described further herein.

A thin oxide liner 46 is formed on the exposed surfaces of the sacrificial layer 40 within the trench. The oxidation may be performed by a plasma oxidation process or other oxidation process that forms a thin oxide layer thereon. The resulting structure is schematically illustrated in FIG. 8. Following such oxidation, the trench 44 is extended through the bottom spacer 38a to the doped III-V compound semiconductor layer 36.

Figure 9:
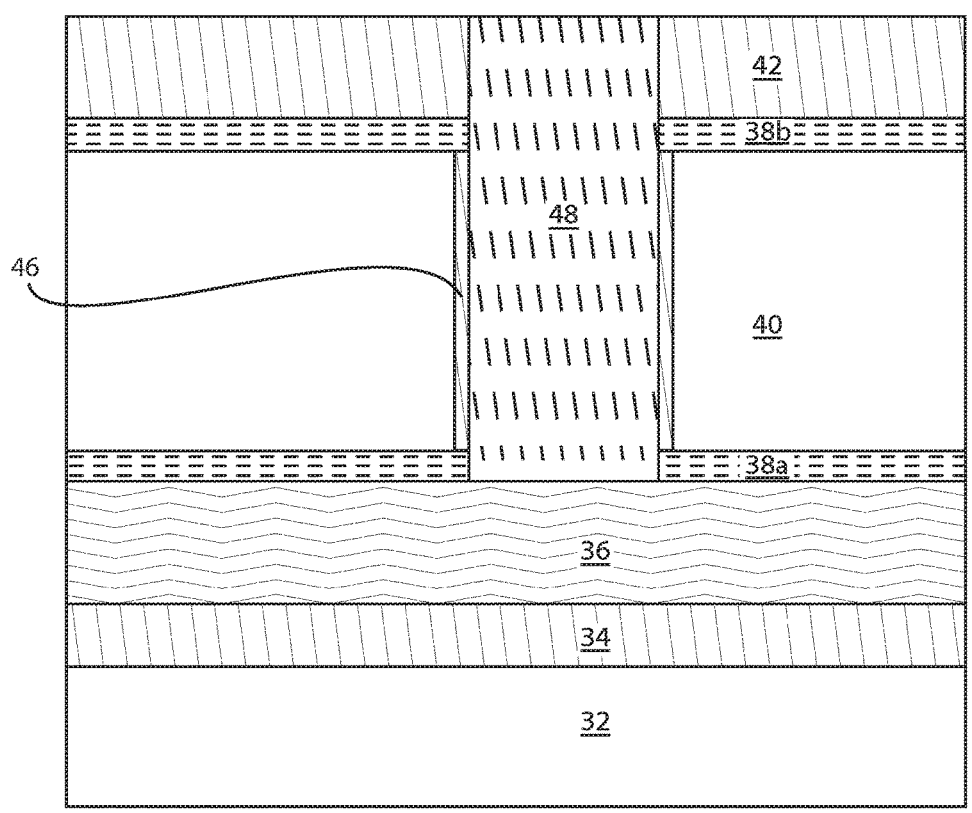
FIG. 9 is a side cross-sectional view depicting epitaxially forming a semiconductor material in the trench of the structure depicted in FIG. 8.

Referring to FIG. 9, a BJT base material 48 is epitaxially grown on the exposed surface of the doped III-V compound semiconductor layer 36 within the trench 44. The base material is lattice-matched to the doped III-V compound semiconductor layer 36 or close to lattice-matching. In the latter case, a strained base may be obtained. The deposited base material may be doped in situ such that it has p-type conductivity, the opposite conductivity type of the semiconductor layer 36. The doping concentration of the base material is between 1e17-1e19 $cm^{-3}$ in the exemplary embodiments. The base material 48 optionally consists essentially of the same III-V material as the layer 36 on which it is formed in some embodiments, for example InGaAs having the same stoichiometry as the underlying layer. A homojunction bipolar junction transistor can be fabricated in such embodiments. A portion of the base material (overgrowth) may extend above the top surface of the oxide layer 42. The structure is polished to remove such overgrowth back to the top surface of the oxide layer, as shown in FIG. 7. Additional oxide material is then deposited and planarized on the structure as shown in FIG. 9, thereby increasing the thickness of the oxide layer 42 such that it covers the exposed surface of the epitaxial base material.

Figure 10:
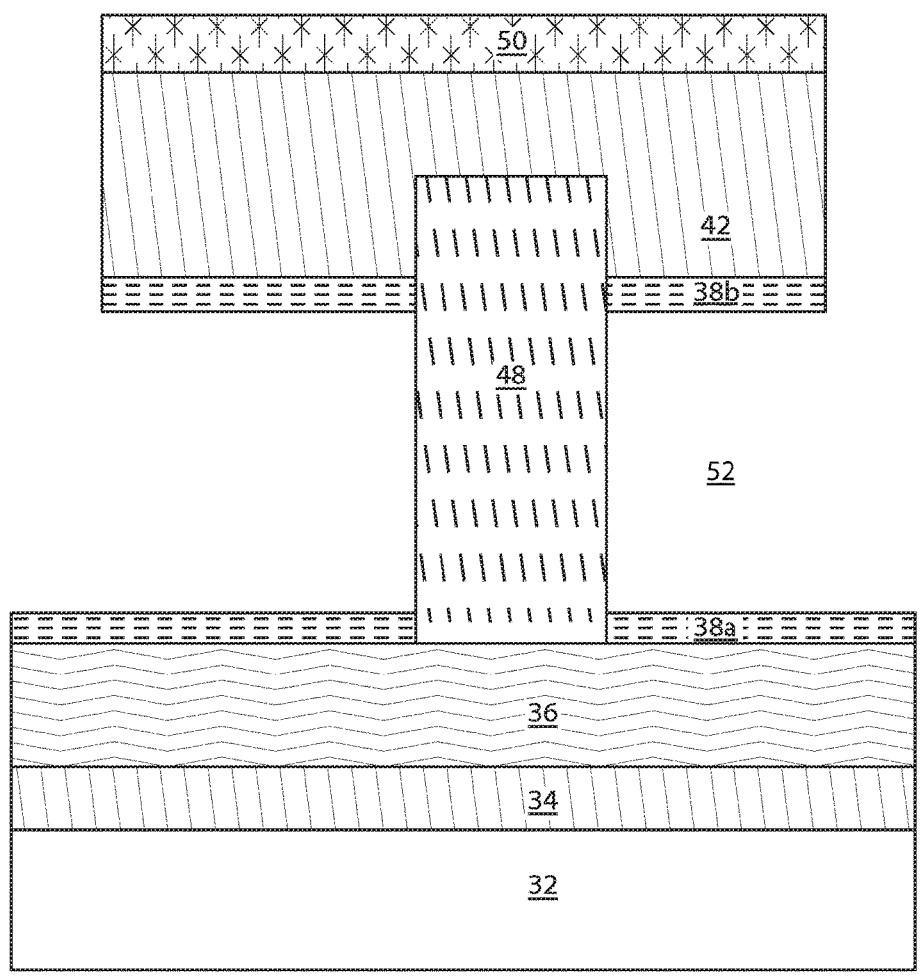
FIG. 10 is a side cross-sectional view depicting removal of a sacrificial material from the structure shown in FIG. 9 to expose sidewalls of the vertically oriented base region.

FIG. 10 depicts removal of a sacrificial material from the structure shown in FIG. 9 to expose sidewalls of the vertically oriented base region, i.e., BJT base 48. A hard mask 50, for example a silicon nitride mask, is deposited on the oxide layer 42. The hard mask 50 overlaps the base region containing the base material 48 on all sides and thereby protects this region and the surrounding region during subsequent processing. The periphery of the oxide layer 42 is exposed. The exposed portion of the oxide layer 42 and the portions of the top spacer 38b and sacrificial layer 40 beneath the exposed portion of the oxide layer are recessed using a sequence of reactive ion etch processes, stopping near but not necessarily on the top surface of the bottom spacer 38a. The last phase of the reactive ion etch may be timed to stop within the sacrificial layer 40.

In some embodiments, the sacrificial layer 40 is removed from the structure to form a space 52 between the bottom and top spacers 38a, 38b. A wet etch using hot ammonia can be introduced to selectively remove the sacrificial layer while leaving the spacers 38a, 38b and the thin oxide liner 46 substantially intact. The thin oxide liner 46 adjoining the base material 48 is then removed to obtain the structure shown in FIG. 10. Such removal can involve using a SiCoNi™ etch, a short HF etch, or any other suitable pre-clean process. A SiCoNi™ etch is a plasma-assisted dry etch process that involves simultaneous exposure of a substrate to hydrogen, $NF_3$ and $NH_3$ plasma by-products.

Figure 11:
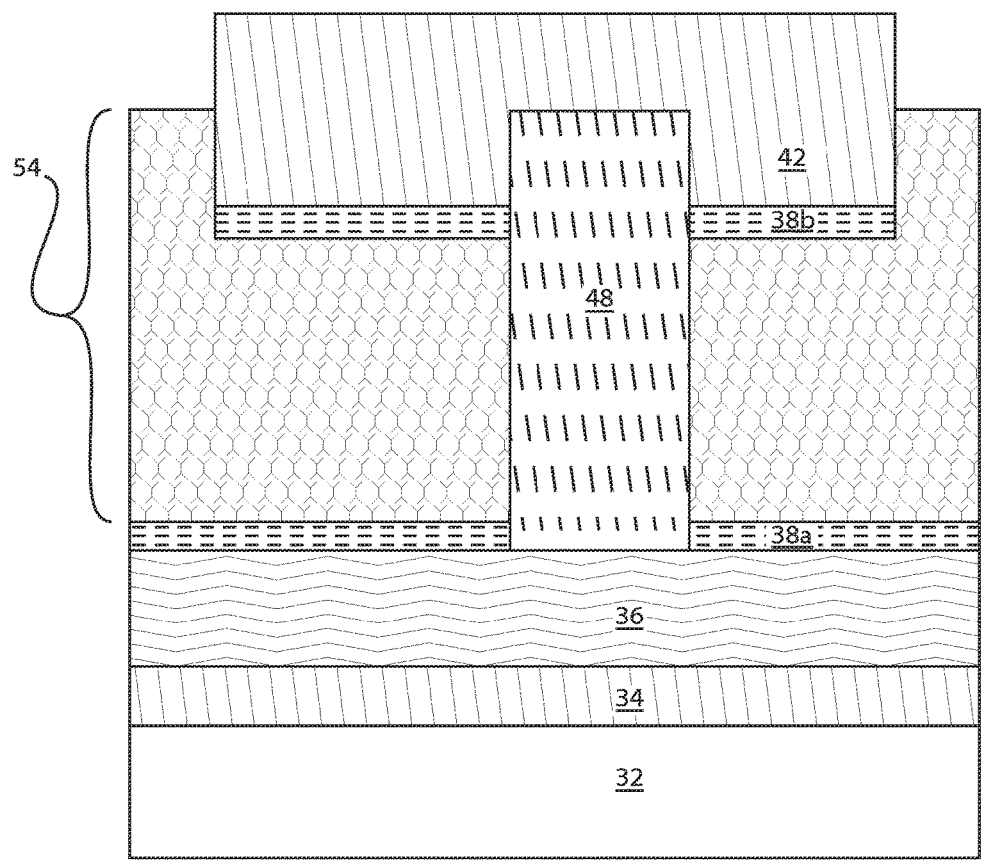
FIG. 11 is a side cross-sectional view depicting epitaxial growth of extrinsic base material on the base region.

A doped, extrinsic base 54 is epitaxially grown within the recess 52 on and all around the exposed III-V base material 48 (the epitaxial base region of a subsequently formed BJT), thereby obtaining a structure as shown in FIG. 11. The doping concentration of the extrinsic base 54 in one or more embodiments is in the range of $4\times10^{19}$ atoms/cm$^3$ to $6\times10^{21}$ atoms/cm$^3$. The extrinsic base epitaxy is highly defective due to lattice mismatch and/or the imperfect exposed surfaces of the base material 48. Exemplary doped extrinsic base materials in some embodiments include silicon, silicon germanium, and germanium. The defective epitaxy, rather than being single crystalline, includes large single crystals with grain boundaries. The extrinsic base 54 is bounded by the bottom and top horizontal spacers 38a, 38b and extends completely around the III-V base material 48 with which it is operatively associated. Large grain polysilicon having p-type conductivity comprises the extrinsic base 54 in an exemplary embodiment where the intrinsic, epitaxial base region is also p-type. Defects within the extrinsic base 54 will not propagate into the base epitaxy (base material 48), which is used as a seed layer, upon epitaxial growth of the extrinsic base 54 thereon. Doped poly-SiGe, doped poly-Ge and doped III-V compound semiconductor materials are among the materials that may alternatively be employed for the extrinsic base 54 of the exemplary structure.

Following formation of the doped, extrinsic base 54, the extrinsic base material is recessed using a reactive ion etch. The hard mask 50 protects the layers beneath it, including the oxide layer 42, the top spacer 38b, the base material 48 and a portion of the extrinsic base 54 around the base material. The bottom spacer 38a functions as an etch stop following removal of the selected portion of the extrinsic base material.

The extrinsic base 54 is further processed to provide the first and second portions 54a, 54b, as depicted in FIGS. 1-2. This can include further photolithography and etch processes.

Figure 12:
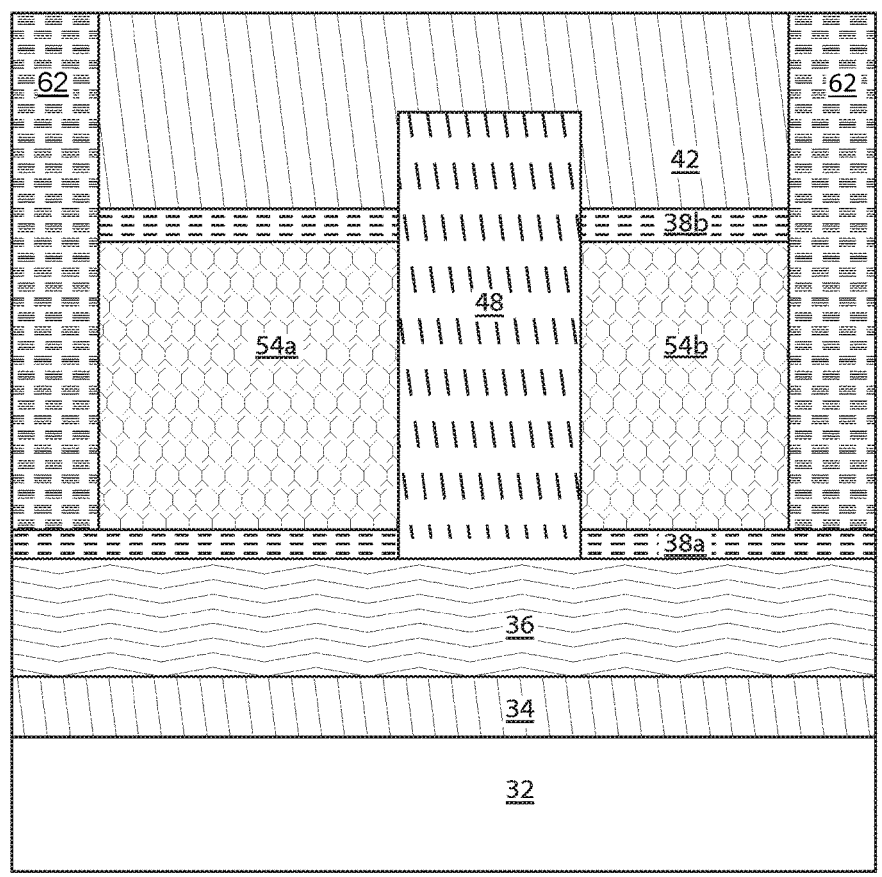
FIG. 12 is a side cross-sectional view depicting patterning the epitaxially semiconductor material to provide the geometry of the extrinsic base region portions of the device, and depositing an interlevel dielectric layer.
Figure 13:
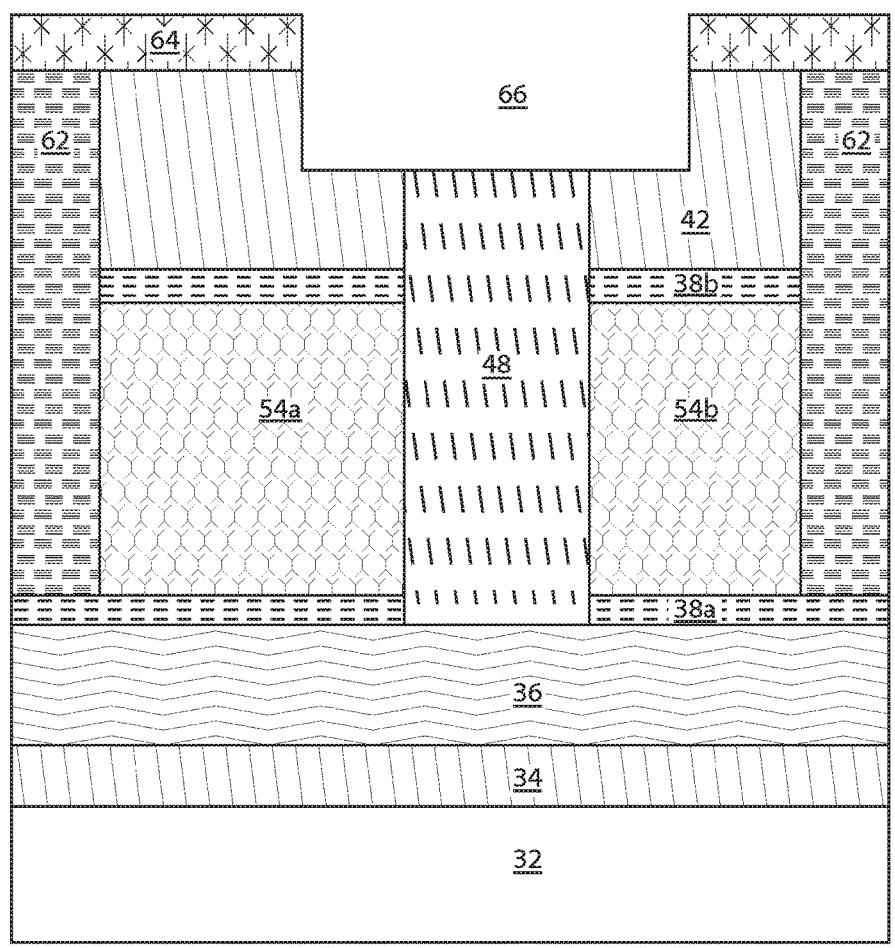
FIG. 13 is a side cross-sectional view of depicting forming a trench that exposes a portion of the vertically oriented base region.

Referring to FIG. 12, an interlayer dielectric (ILD) layer 62, for example silicon dioxide or a low-k dielectric such as SiOCH, is formed on the structure using CVD or other known techniques. The ILD layer 62 may be formed from other dielectric materials, including but not limited to, spin-on-glass, a flowable oxide, a high density plasma oxide, borophosphosilicate glass (BPSG), or any combination thereof. The ILD layer is deposited by any suitable deposition process, including, but not limited to CVD, PVD, plasma-enhanced CVD, atomic layer deposition (ALD), evaporation, chemical solution deposition, or like processes. The outer surfaces of the doped, extrinsic base 54 are protected by the ILD layer. The ILD layer 62 is planarized using chemical mechanical planarization (CMP), as known in the art, down to the top surface of the hard mask 50. The hard mask 50 over the base region is removed and the top surface is planarized to obtain the structure shown in FIG. 12.

A second hard mask 64 is then deposited and patterned on the top surface of the structure depicted in FIG. 12. The second hard mask includes an opening above the base region while protecting other regions of the structure. Using the second hard mask 64, a recess 66 is formed in the structure that extends through the oxide layer 42 down to the top spacer 38B. The portion of the III-V base material 48 extending above the top spacer 38B is also removed. A reactive ion etch (RIE) may be employed to selectively remove the oxide material and the III-V material therein. Etching of the III-V material is timed or otherwise controlled to avoid removing III-V material beneath the top spacer 38B. The etch is selective to the top spacer material, which is silicon nitride in the exemplary embodiment.

Figure 14:
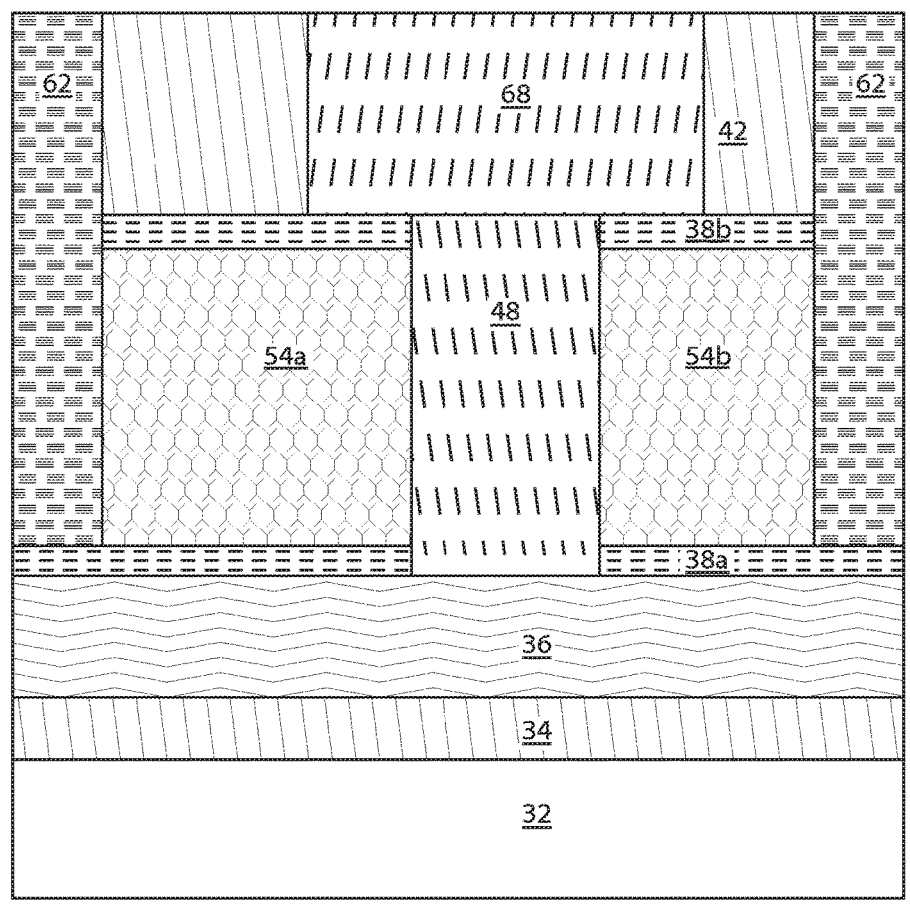
FIG. 14 is a side cross-sectional view depicting following epitaxial growth of collector material within the trench depicted in FIG. 13, in accordance with one embodiment of the present disclosure.

Referring to FIG. 14, a second (top) heavily doped III-V compound semiconductor layer 68 that functions as a BJT collector is epitaxially grown on the exposed top surface of the base material 48 and within the recess 66. The dopants in the second semiconductor layer 68 of the BJT may be incorporated in situ using appropriate precursors, as known in the art. The epitaxy may be essentially polycrystalline rather than single crystal due to surface imperfections of the base material 48 on which the semiconductor layer 68 is grown. Defects in the top III-V compound semiconductor layer 68 may further arise due to lateral growth along the top spacer 38B and along the sidewalls of the oxide layer 42. Defects within the large grain epitaxy will not, however, propagate into the underlying base epitaxy. In one exemplary embodiment, a heavily doped polycrystalline InGaAs layer grown on the base material 48 has a doping concentration of $1e^{19}$-3e20 cm$^{-3}$ or greater and n-type conductivity. The second hard mask 64 is removed and the structure is optionally planarized to obtain the structure schematically shown in FIG. 14.

In a following process sequence, the sample trench 300 is formed exposing a sidewall of the second portion 54b of the extrinsic base 54. If not previously formed, ILD material for an ILD layer 62 is deposited on the structure. Thereafter, the sample trench 300 is formed using photolithography and etching. Specifically, a pattern is produced by applying a photoresist to the surface to be etched; exposing the photoresist to a pattern of radiation; and then developing the pattern into the photoresist utilizing a resist developer. Once the patterning of the photoresist is completed, the sections covered by the photoresist are protected while the exposed regions are removed using a selective etching process that removes the unprotected regions. For example, the exposed portions of the ILD layer 62 may be removed with an anisotropic etch, such as reactive ion etching (RIE). The etch process may be selective to the lower spacer level 38a, and exposes a sidewall of the second portion 54b of the extrinsic base.

Figure 15:
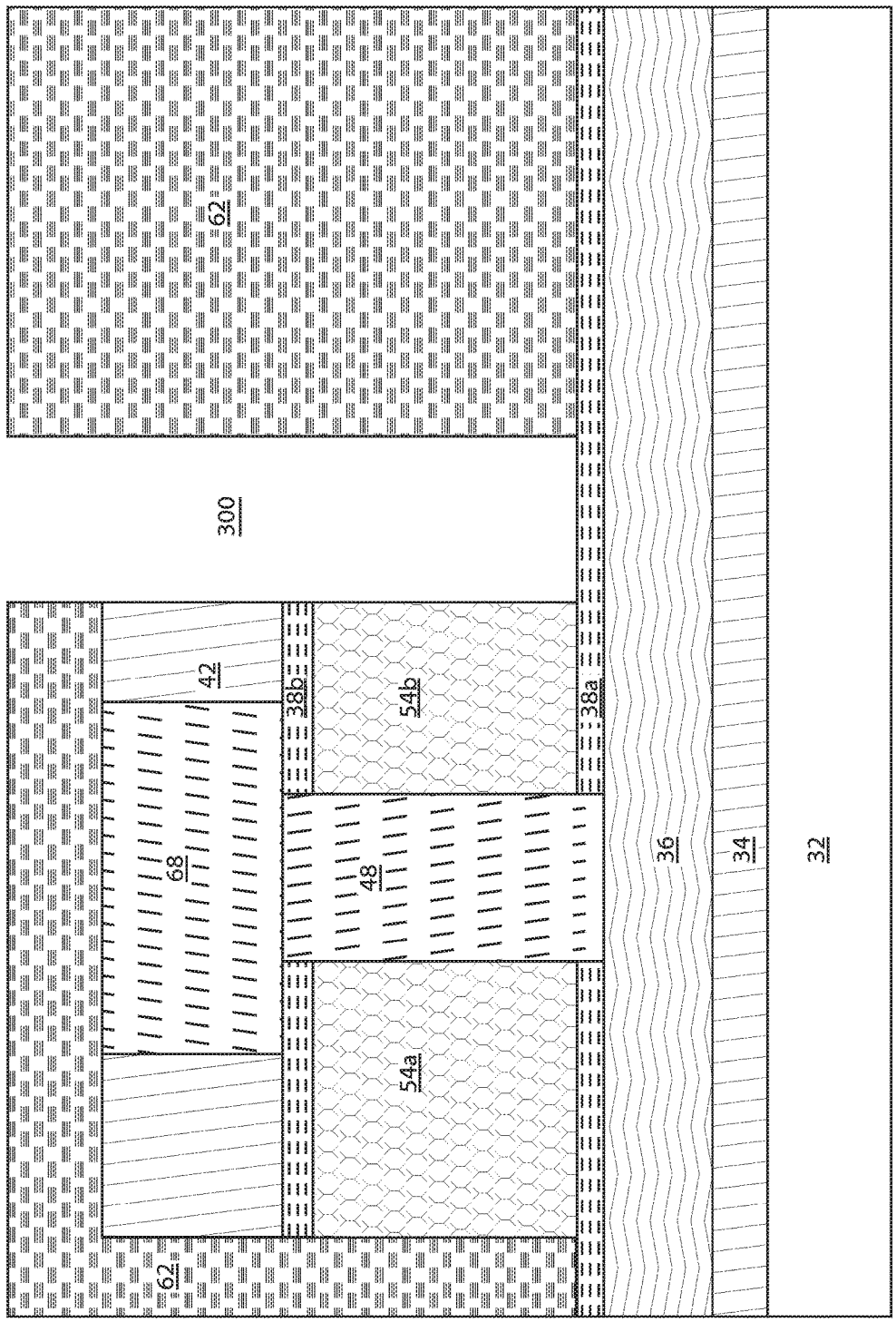
FIG. 15 is a side cross-sectional view deposition of an interlayer dielectric (ILD) layer on the structure depicted in FIG. 14, and forming a sample trench exposing a sidewall of an extrinsic base region portion of the device.
Figure 16:
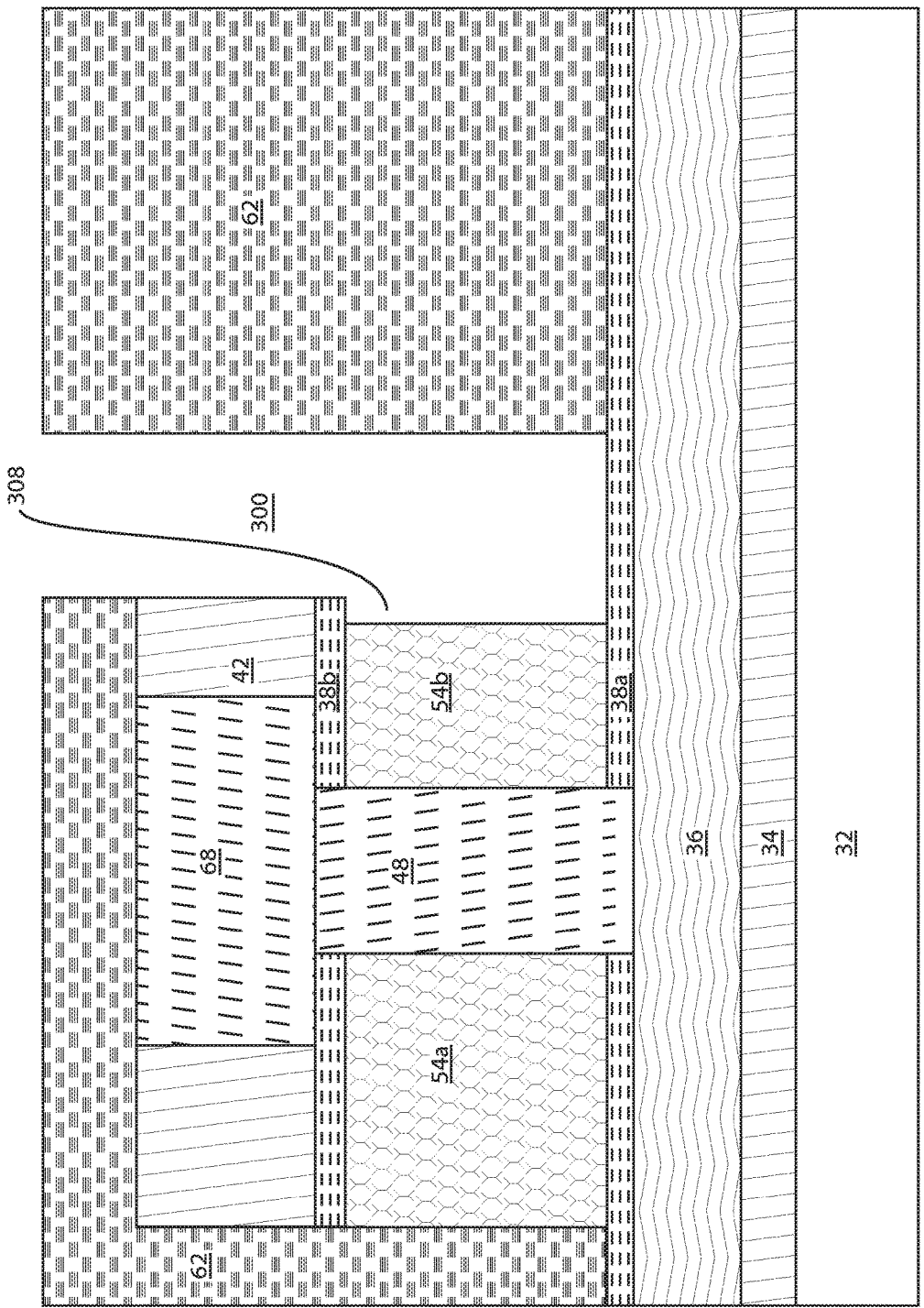
FIG. 16 is a side cross-sectional view depicting one embodiment of a lateral etch process to laterally etching the extrinsic base region of the structure depicted in FIG. 15 forming an undercut region.

FIG. 16 depicting one embodiment of a lateral etch process to laterally etching the extrinsic base region of the structure depicted in FIG. 15 forming an undercut region 308. More specifically, the second portion of the extrinsic base region 54b may be laterally etched by an isotropic etch process that removes the material of the extrinsic base region 54b selectively to at least the lower spacer layer 38a, the interlevel dielectric layer 62 and the collector level dielectric 42. For example, when the extrinsic base region 54b is composed of silicon, the lateral etch may be a KOH based wet etch.

Figure 17:
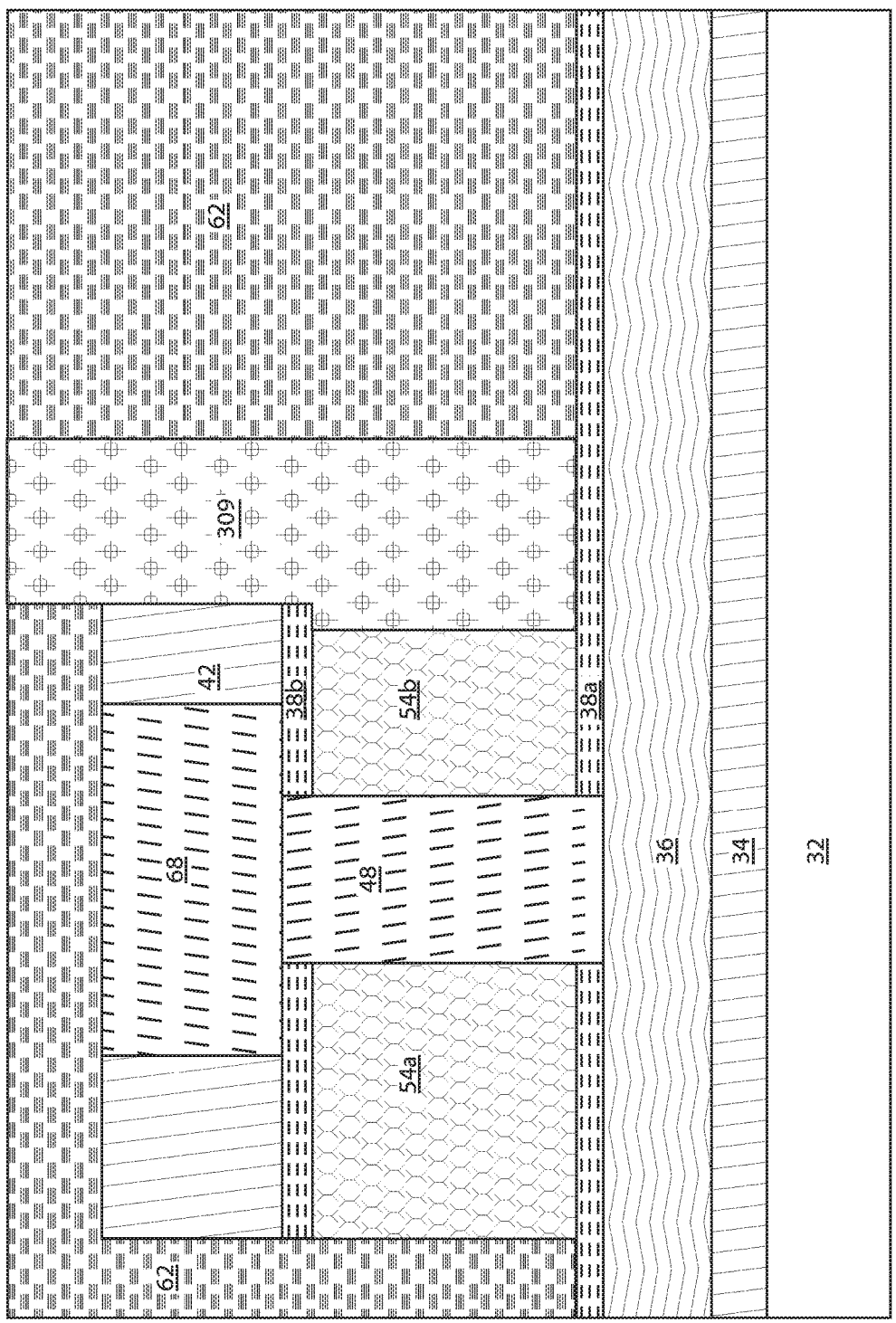
FIG. 17 is a side cross-sectional view of depositing at least one metal filling the trench, as well as the undercut region, depicted in FIG. 16.

FIG. 17 depicts one embodiment of depositing at least one metal containing material 309 within the sample trench 300, as well as the undercut region 308. The at least one metal containing material 309 that is deposited in the undercut region 308 may be composed of titanium nitride (TIN), gold (Au), silver chloride (AgCl) or other material that can provide the sensing surface 200, 201, as described with reference to FIGS. 1-4. The at least one metal containing material 309 may be deposited using a chemical vapor deposition, e.g., plasma enhanced chemical vapor deposition (PECVD), and/or an atomic layer deposition (ALD) process. For example, a complete metal fill may be provided by atomic layer deposition (ALD) titanium nitride (TiN), or conformal liner deposition by ALD TiN that is followed by metal fill using chemical vapor deposition (CVD) titanium nitride (TiN). In some embodiments, an optional post-deposition annealing process may be applied. In some embodiments, the deposition of the at least one metal containing material 309 is followed by a planarization process to remove any metal material that overburdens/overfills the sample trench 300. In some embodiments, the planarization process is provided by chemical mechanical planarization (CMP).

Figure 18:
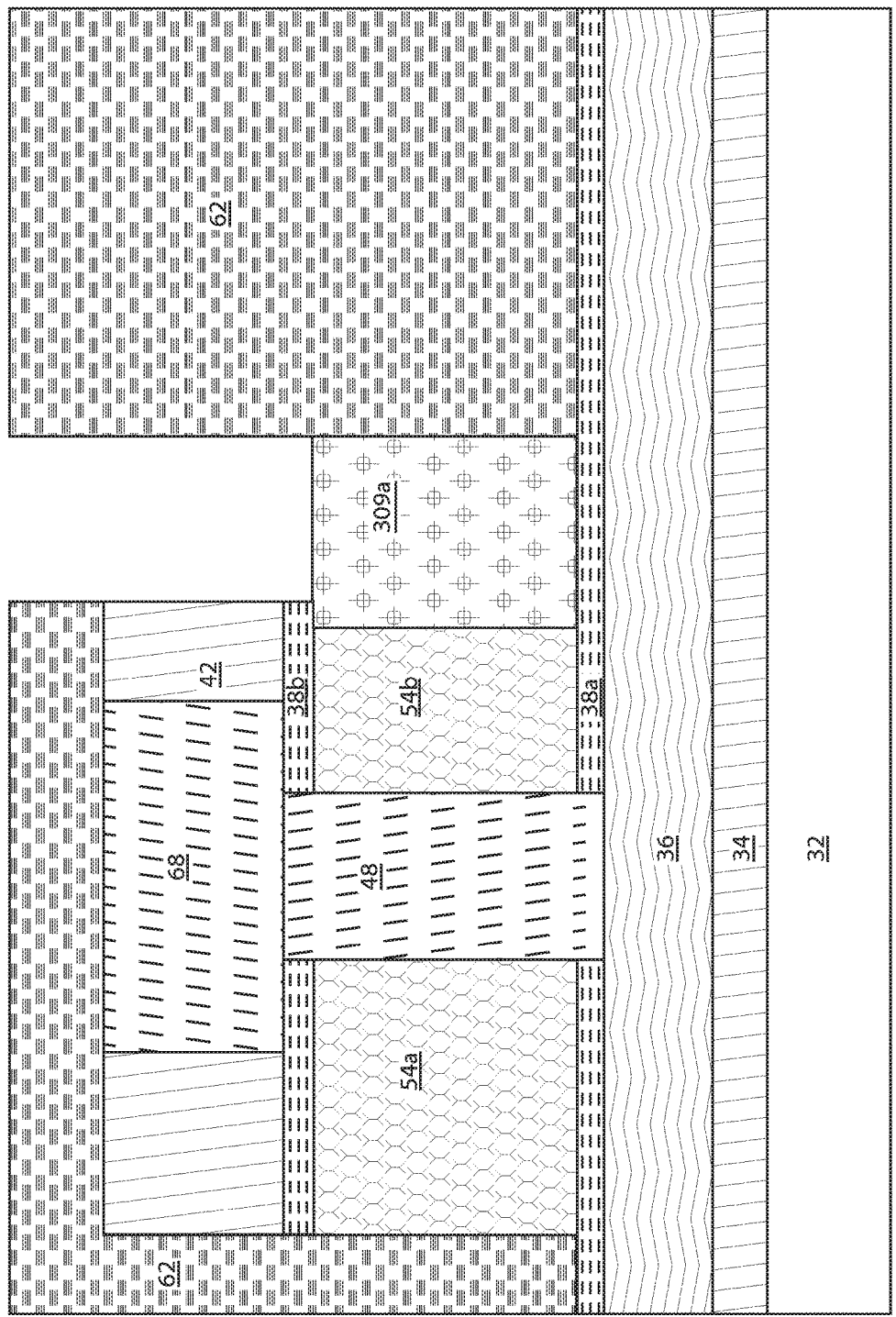
FIG. 18 is a side cross-sectional view depicting recessing a portion of the metal that is present within the trench, in accordance with one embodiment of the present disclosure.

FIG. 18 depicts recessing a portion of the metal 309 that is present within the sample trench 300. In some embodiments, the metal 309 is first recessed with an isotropic wet etch. For example, when the metal 309 is composed of titanium nitride (TiN), the etch process for recessing the titanium nitride may be an isotropic wet etch that is, e.g., Cl-based, or $H_2O_2/NH_4OH$-based. The height of the recessed metal 309a may be substantially equal to the height that corresponds to the upper surface of the undercut region 308. It is noted that the above etch composition provides only one example of an etch process that may be employed at this stage of the process flow, and that other compositions are equally applicable. For example, etch composition for etching gold (Au) or silver chloride (AgCl) may be employed when the sensing surface 200, 201 being formed is composed of gold (Au) or silver chloride (AgCl).

Figure 19:
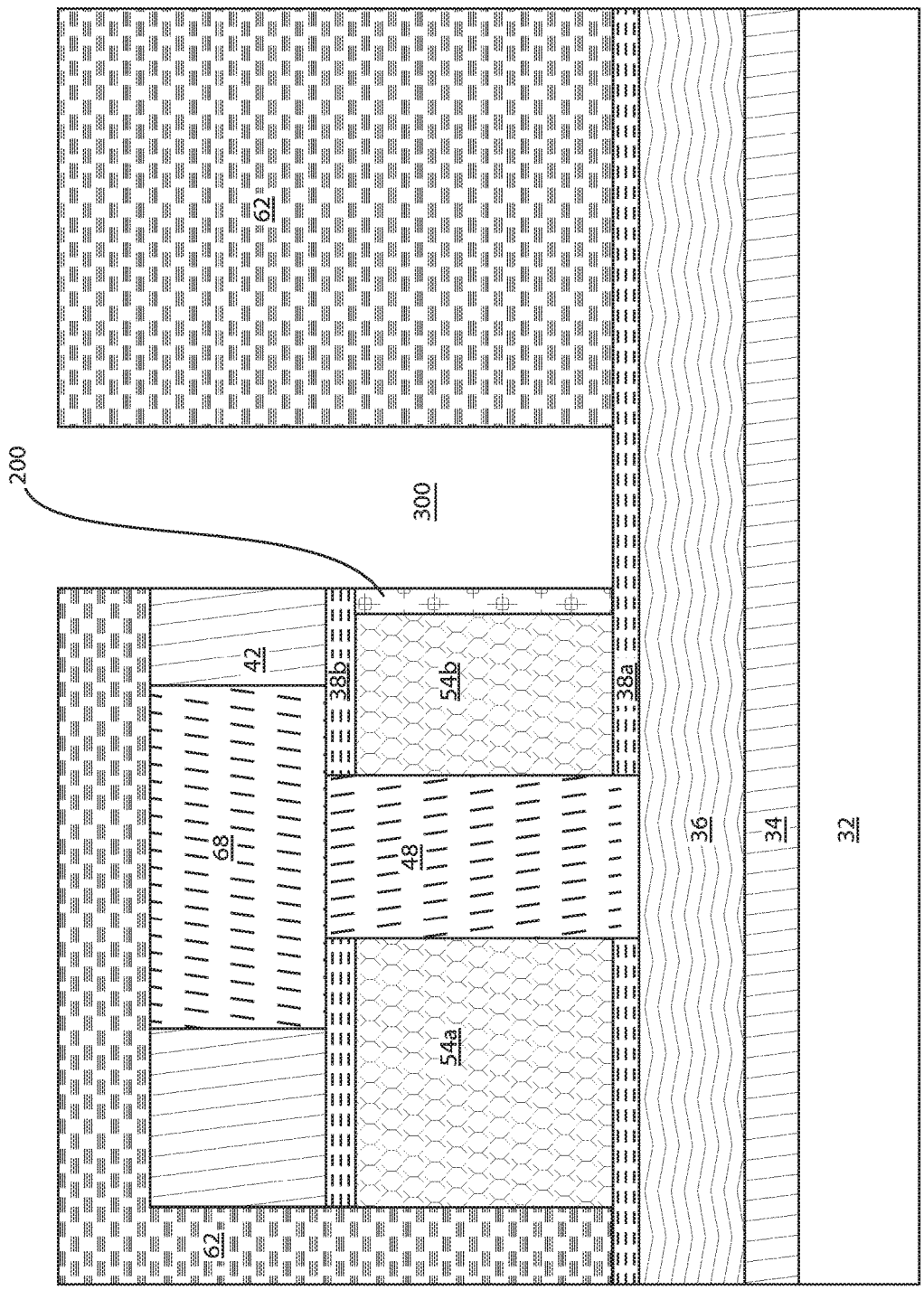
FIG. 19 is a side cross-sectional view depicting applying an anisotropic etch process to the recessed metal that is present within the trench, wherein the anisotropic etch process removes a majority of the metal, while a remainder of the metal is present in the undercut region to provide the sensing element of the BJT sensor, in accordance with one embodiment of the present disclosure.

FIG. 19 depicts applying an anisotropic etch process to the recessed metal 309a that is present within the sample trench 300. The anisotropic etch process removes a majority of the metal, while a remainder of the metal is present in the undercut region 308 to provide the sensing element 200, 201 of the BJT sensor. As used herein, an "anisotropic etch process" denotes a material removal process in which the etch rate in the direction normal to the surface to be etched is greater than in the direction parallel to the surface to be etched. In one embodiment, the anisotropic etch process removes all the metal 309 that is present within the sample trench 300 except for the portion within the undercut region 308 that is protected by the overlying portions of the upper spacer layer 38b, the overlying portions of the collector level dielectric layer 42, and the overlying portions of the ILD 62. Because of the anisotropic nature of the etch process, the remaining portion of the metal present in the undercut region 308 that provides the sensing surface 200, 201 and provides a sidewall that is aligned with the first sidewall S1 of the sample trench 300 provided by the overlying portions of the upper spacer layer 38b, the overlying portions of the collector level dielectric layer 42, and the overlying portions of the ILD 62.

In some embodiments, the anisotropic etch that is employed at this stage of the process flow includes reactive ion etching. Reactive Ion Etching (RIE) is a form of plasma etching in which during etching the surface to be etched is placed on the RF powered electrode. Moreover, during RIE the surface to be etched takes on a potential that accelerates the etching species extracted from plasma toward the surface, in which the chemical etching reaction is taking place in the direction normal to the surface.

In some embodiments, when the recessed metal 309a is composed of titanium nitride, the reactive ion etch process may employ Cl-based etch chemistries, such as $Ar/Cl_2$, or $Xe/Cl_2$. Other examples of anisotropic etching that can be used at this point of the present invention include ion beam etching, plasma etching or laser ablation.

Referring to FIGS. 1 and 2, the emitter, base and collector contacts 82, 84, 86 are the formed. Photolithographic and etching techniques known to the art may be employed to form trenches within the ILD layer and other layers prior to metal deposition. Contact material may, for example, include aluminum (Al), platinum (Pt), gold (Au), tungsten (W), titanium (Ti), palladium (Pd) or any combination thereof. Exemplary processes for depositing contact material include CVD, PECVD, PVD, plating, thermal or e-beam evaporation, or sputtering. A planarization process, for example, CMP, is performed to remove any electrically conductive material from the top surface of the ILD layer.

It is to be appreciated that the various layers and/or regions shown in the accompanying figures may not be drawn to scale. Furthermore, one or more layers of a type commonly used in such integrated circuit devices may not be explicitly shown in a given figure for ease of explanation. This does not imply that the layer(s) not explicitly shown are omitted in the actual integrated circuit device.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A bipolar junction transistor containing sensor comprising:
   a vertically oriented stack of an emitter overlying a supporting substrate, a vertically oriented base region present directly atop the emitter and a collector atop the base region;
   a first extrinsic base region in contact with a first sidewall of the vertically oriented base region, wherein the first extrinsic base region is electrically contacted to provide a bias current of the bipolar junction transistor during sensor operation;
   a second extrinsic base region in contact with a second sidewall of the base region, the second extrinsic base region including a sensing element; and
   a sample trench having a trench sidewall provided by the sensing element.

2. The bipolar junction transistor containing sensor of claim 1, wherein the sensing element that provides the trench sidewall extends an entire height of the second extrinsic base region.

3. The bipolar junction transistor containing sensor of claim 1, wherein the sensing element is a titanium nitride layers, the sensing element being for sensing PH of a sample within the sample trench.

4. The bipolar junction transistor containing sensor of claim 1, wherein the sensing element is comprised of silver chloride, the sensing element being for sensing chloride content of a sample within the sample trench.

5. The bipolar junction transistor containing sensor of claim 1, wherein the sensing element is comprised of gold, the sensing element being for sensing proteins using thio chemistry.

6. A sensor comprising:
a sample trench;
a first vertically oriented bipolar junction transistor doped to a first conductivity type, the first vertically oriented bipolar junction transistor having a first sensing surface of a first extrinsic base region providing a first sidewall of the sample trench; and
a second vertically oriented bipolar junction transistor doped to a second conductivity type, the second vertically oriented bipolar junction transistor having a second sensing surface of a second extrinsic base region providing a second sidewall of the sample trench.

7. The sensor of claim 6, wherein the first conductivity type is n-type and the second conductivity type is p-type.

8. The sensor of claim 6, wherein the first sensing surface extends an entire height of the first extrinsic base region.

9. The sensor of claim 8, wherein the first sensing surface has a composition selected from the group consisting of titanium nitride (TiN), silver chloride a (AgCl), gold (Au), and combinations thereof.

10. The sensor of claim 6, wherein the second sensing surface extends an entire height of the second extrinsic base region.

11. The sensor of claim 10, wherein the second sensing surface has a composition selected from titanium nitride (TiN), silver chloride (AgCl), gold (Au), and combinations thereof.

12. A method of forming a sensor comprising:
forming a bipolar junction transistor including a vertically oriented base region, and a two-component extrinsic base region;
forming a sample trench exposing a sidewall of a first component of the two-component extrinsic base region; and
forming a sensor surface on the sidewall of the first component of the extrinsic base region that is opposite a sidewall of the first component of the extrinsic base region that is in contact with the vertically oriented base region.

13. The method of claim 12, wherein said forming the sample trench comprises depositing at least one dielectric layer on the bipolar junction transistor, and etching the sample trench into the at least one dielectric layer.

14. The method of claim 13, wherein said forming the sensor surface on the sidewall of the first component of the extrinsic base region comprises applying a lateral etch to the sidewall of the first component of the extrinsic base region to form an undercut region present underlying the at least one dielectric layer; and filling the undercut region with a metal-containing material.

15. The method of claim 14, wherein the metal-containing material that provides the sensor surface is selected from the group consisting of titanium nitride (TiN), silver chloride (AgCl), gold (Au), and combinations thereof.

16. The method of claim 14, wherein said filling the undercut region comprises atomic layer deposition (ALD) of the metal-containing material.

17. The method of claim 16, wherein following said filling the undercut region, an etch process removes the metal-containing material that overfills the undercut region.

18. The method of claim 17, wherein the etch process that removes the metal-containing material that overfills the undercut region is an anisotropic etch.

19. The method of claim 18, wherein the anisotropic etch is reactive ion etching.

20. The method of claim 18, wherein a second component of the two-component extrinsic base region that is separate from the first component of the two-component extrinsic base region is electrically contacted to provide a bias current of the bipolar junction transistor during sensor operation.

* * * * *